United States Patent [19]
Su et al.

[11] Patent Number: 5,919,693
[45] Date of Patent: Jul. 6, 1999

[54] **NUCLEIC ACID SEQUENCES AND EXPRESSION SYSTEMS FOR HEPARINASE II AND HEPARINASE III DERIVED FROM *FLAVOBACTERIUM HEPARINUM***

[75] Inventors: Hongsheng Su, Lonqnenil, Canada; Francoise Blain, Qué, Canada; Clark Bennett; Kangfu Gu, both of Quebec, Canada; Joseph Zimmermann, Elm Grove, Wis.; Roy Musil, Carlsbad, Calif.

[73] Assignee: IBEX Technologies Corp., Malvern, Pa.

[21] Appl. No.: 08/900,951

[22] Filed: Jul. 25, 1997

Related U.S. Application Data

[62] Division of application No. 08/258,639, Jun. 10, 1994, Pat. No. 5,681,733.

[51] Int. Cl.⁶ .............................. C12N 15/60; C12N 1/21; C12N 15/63; C12N 9/88
[52] U.S. Cl. .................... 435/252.3; 536/23.2; 536/24.1; 435/320.1; 435/252.33; 435/232
[58] Field of Search .................................. 536/23.2, 24.1; 435/320.1, 252.3, 252.33, 232

[56] References Cited

U.S. PATENT DOCUMENTS

| 5,169,772 | 12/1992 | Zimmerman et al. | 435/232 |
| 5,262,325 | 11/1993 | Zimmerman et al. | 435/269 |

FOREIGN PATENT DOCUMENTS

| WO 9308289 | 4/1993 | WIPO. |
| WO 9412618 | 6/1994 | WIPO. |

OTHER PUBLICATIONS

Choay et al. (1980) *Thrombosis Res.* 18:573–578.
Turnbull et al. (1992) *J. Biol. Chem.* 267:10337–10341.
Kjellen et al. (1991) *Ann. Rev. Biochem.* 60:443–475.
Burgess et al. (1989) *Ann. Rev. Biochem.* 58:575–606.
McClean (1916) *Am. J. Physiol.* 41:250–257.
Linhardt et al. (1986) *Appl. Biochem. Biotechnol.* 12:135–177.
Oldberg et al. (1980) *Biochemistry* 19:5755–5762.
Nakajima et al. (1984) *J. Biol. Chem.* 259:2283–2290.
Gaal et al. (1989) *Biochem. Biophys. Res. Comm.* 161:604–614.
Nakajuma et al. (1988) *J. Cell. Biochem.* 36:157–167.
Yang et al. (1985) *J. Biol. Chem.* 260(3):1849–1857.
Lohse et al. (1992) *J. Biol. Chem.* 267:24347–24355.
Desai et al. (1993) *Arch. Biochem. Biophys.* 306(2):461–468.
Bashkin et al. (1992) *J. Cell Physiol.* 151:126–137.
Chappell et al. *J. Biol. Chem.* 268(19):14168–14175.
St. Groth et al. (1980) *J. Immunol. Methods* 35:1–21.
Lutz et al. (1988) *Exp. Cell. Res.* 175:109–124.
Sternberger et al. (1970) *J. Histochem. Cytochem.* 18:315–333.
Bayer et al. (1979) *Meth. Enzym.* 62:308–315.
Engvall et al. (1972) *Immunol.* 109:129–135.
Goding (1976) *J. Immunol. Meth.* 13:215–226.
Galliher et al. (1981) *Appl. Environ. Microbiol.* 41(2):360–365.
Laemmli (1970) *Nature* 227:680–685.
Brosius et al. (1984) *Proc. Natl. Acad. Sci. USA* 81:6929–6993.
Shine et al. (1974) *Proc. Natl. Acad. Sci. USA* 71:1342–1346.
Baker et al. (1984) *Proc. Natl. Acad. Sci.* 81:6779–6783.
Sanger et al. (1978) *Proc. Natl. Sci.* 74:5463–5467.
Southern (1975) *J. Mol. Biol.* 98:503–517.
Yanisch–Perron et al. (1985) *Gene* 33:103–119.
Vierra et al. (1991) *Gene* 100:189–194.
Chang et al. (1978) *J. Bact.* 134:1141–1156.
Lohse, et al., The Journal of Biological Chemistry, vol. 267:34, pp. 24347–24355 (1992).
Sasisekharan, et al., Proc. Natl. Acad. Sci., USA, vol. 90, pp. 3660–3664 (1993).
Zimmermann, et al., Applied and Environmental Microbiology, vol. 56:11, pp. 2593–3594 (1990).

*Primary Examiner*—Rebecca E. Prouty
*Attorney, Agent, or Firm*—Hale & Dorr LLP

[57] ABSTRACT

The present invention describes the isolation and sequence of genes from *Flavobacterium heparinum* encoding heparin and heparan sulfate degrading enzymes, heparinase II and heparinase III (EC 4.2.2.8). It further describes a method of expressing and an expression for heparinases I, II and III using a modified ribosome binding region derived from a promoter from glycosaminoglycan lyase genes of *F. heparinum*. Also, a multi-step protein purification method incorporating cell disruption, cation exchange chromatography, affinity chromatography and hydroxylapatite chromatography is outlined. Antibodies against a post-translational modification moiety common to *Flavobacterium heparinum* proteins and a method to obtain antibodies specific to these moieties and to the amino acid sequences of heparinases I, II and III are described.

12 Claims, 11 Drawing Sheets pBhep    AGGAAACAGAATTCATG

S-D    10nt pGhep    AGGAGACAGAATTCATG

S-D    9nt pΔ4hep   AGGAGAATTCATG

S-D    5 nt pGB      AGGAGACAGGATCC

S-D    BamHI

FIG. 1

| | |
|---|---|
| ATGAAAAGAC AATTATACCT GTATGTGATT TTTGTTGTAG TTGAACTTAT GGTTTTTACA | 60 |
| ACAAAGGGCT ATTCCCAAAC CAAGGCCGAT GTGGTTTGGA AAGACGTGGA TGGCGTATCT | 120 |
| ATGCCCATAC CCCCTAAGAC CCACCCGCGT TTGTATCTAC GTGAGCAGCA AGTTCCTGAC | 180 |
| CTGAAAAACA GGATGAACGA CCCTAAACTG AAAAAAGTTT GGGCCGATAT GATCAAGATG | 240 |
| CAGGAAGACT GGAAGCCAGC TGATATTCCT GAAGTTAAAG ACTTTCGTTT TTATTTTAAC | 300 |
| CAGAAAGGGC TTACTGTAAG GGTTGAACTA ATGGCCCTGA ACTATCTGAT GACCAAGGAT | 360 |
| CCAAAGGTAG GACGGGAAGC CATCACTTCA ATTATTGATA CCCTTGAAAC TGCAACTTTT | 420 |
| AAACCAGCAG GTGATATTTC GAGAGGGATA GGCCTGTTTA TGGTTACAGG GGCCATTGTG | 480 |
| TATGACTGGT GCTACGATCA GCTGAAACCA GAAGAGAAAA CACGTTTTGT GAAGGCATTT | 540 |
| GTGAGGCTGG CCAAAATGCT CGAATGTGGT TATCCTCCGG TAAAAGACAA GTCTATTGTT | 600 |
| GGGCATGCTT CCGAATGGAT GATCATGCGG GACCTGCTTT CTGTAGGGAT TGCCATTTAC | 660 |
| GATGAATTCC CTGAGATGTA TAACCTGGCT GCGGGTCGTT TTTTCAAAGA ACACCTGGTT | 720 |
| GCCCGCAACT GGTTTTATCC CTCGCATAAC TACCATCAGG GTATGTCATA CCTGAACGTA | 780 |
| AGATTTACCA ACGACCTTTT TGCCCTCTGG ATATTAGACC GGATGGGCGC TGGTAATGTG | 840 |
| TTTAATCCAG GGCAGCAGTT TATCCTTTAT GACGCGATCT ATAAACGCCG CCCCGATGGA | 900 |
| CAGATTTTAG CAGGTGGAGA TGTAGATTAT TCCAGGAAAA AACCAAAATA TTATACGATG | 960 |
| CCTGCATTGC TTGCAGGTAG CTATTATAAA GATGAATACC TTAATTACGA ATTCCTGAAA | 1020 |
| GATCCCAATG TTGAGCCACA TTGCAAATTG TTCGAATTTT TATGGCGCGA TACCCAGTTG | 1080 |
| GGAAGTCGTA AGCCTGATGA TTTGCCACTT TCCAGGTACT CAGGATCGCC TTTTGGATGG | 1140 |
| ATGATTGCCC GTACCGGATC GGGTCCGGAA AGTGTGATTG CAGAGATGAA AGTCAACGAA | 1200 |

FIG.4A

```
TATTCCTTTC TTAACCATCA GCATCAGGAT GCAGGAGCCT TCCAGATCTA TTACAAAGGC    1260
CCGCTGGCCA TAGATGCAGG CTCGTATACA GGTTCTTCAG GAGGTTATAA CAGTCCGCAC    1320
AACAAGAACT TTTTTAAGCG GACTATTGCA CACAATAGCT TGCTGATTTA CGATCCTAAA    1380
GAAACTTTCA GTTCGTCGGG ATATGGTGGA AGTGACCATA CCGATTTTGC TGCCAACGAT    1440
GGTGGTCAGC GGCTGCCCGG AAAAGGTTGG ATTGCACCCC GCGACCTTAA AGAAATGCTG    1500
GCAGGCGATT TCAGGACCGG CAAAATTCTT GCCCAGGGCT TTGGTCCGGA TAACCAAACC    1560
CCTGATTATA CTTATCTGAA AGGAGACATT ACAGCAGCTT ATTCGGCAAA AGTGAAGGAA    1620
GTAAAACGTT CATTTCTATT CCTGAACCTT AAGGATGCCA AAGTTCCGGC AGCGATGATC    1680
GTTTTTGACA AGGTAGTTGC TTCCAATCCT GATTTTAAGA AGTTCTGGTT GTTGCACAGT    1740
ATTGAGCAGC CTGAAATAAA GGGGAATCAG ATTACCATAA AACGTACAAA AAACGGTGAT    1800
AGTGGGATGT TGGTGAATAC GGCTTTGCTG CCGGATGCGG CCAATTCAAA CATTACCTCC    1860
ATTGGCGGCA AGGGCAAAGA CTTCTGGGTG TTTGGTACCA ATTATACCAA TGATCCTAAA    1920
CCGGGCACGG ATGAAGCATT GGAACGTGGA GAATGGCGTG TGGAAATCAC TCCAAAAAAG    1980
GCAGCAGCCG AAGATTACTA CCTGAATGTG ATACAGATTG CCGACAATAC ACAGCAAAAA    2040
TTACACGAGG TGAAGCGTAT TGACGGTGAC AAGGTTGTTG GTGTGCAGCT TGCTGACAGG    2100
ATAGTTACTT TTAGCAAAAC TTCAGAAACT GTTGATCGTC CCTTTGGCTT TTCCGTTGTT    2160
GGTAAAGGAA CATTCAAATT TGTGATGACC GATCTTTTAG CGGGTACCTG GCAGGTGCTG    2220
AAAGACGGAA AAATACTTTA TCCTGCGCTT TCTGCAAAAG GTGATGATGG ACCCCTTTAT    2280
TTTGAAGGAA CTGAAGGAAC CTACCGTTTT TTGAGATAA                           2319
```

FIG.4B

MKRQLYLYVI FVVVELMVFT TKGYSQTKAD VVWKDVDGVS MPIPPKTHPR LYLREQQVPD

KPADIP EVKDFR
LKNRMNDPKL KKVWADMIKM QEDWKPADIP EVKDFRFYFN QKGLTVRVEL MALNYLMTKD
*PEPTIDE 2B*

PKVGREAITS IIDTLETATF KPAGDISRGI GLFMVTGAIV YDWCYDQLKP EEKTRFVKAF

EFPEMYNLA AGR
VRLAKMLECG YPPVKDKSIV GHASEWMIMR DLLSVGIAIY DEFPEMYNLA AGRFFKEHLV
*PEPTIDE 2A*

ARNWFYPSHN YHQGMSYLNV RFTNDLFALW ILDRMGAGNV FNPGQQFILY DAIYKRRPDG

QILAGGDVDY SRKKPKYYTM PALLAGSYYK DEYLNYEFLK DPNVEPHCKL FEFLWRDTQL

GSRKPDDLPL SRYSGSPFGW MIARTGWGPE SVIAEMKVNE YSFLNHQHQD AGAFQIYYKG

PLAIDAGSYT GSSGGYNSPH NKNFFKRTIA HNSLLIYDPK ETFSSSGYGG SDHTDFAAND

L AGDFVTGKIL AQGFGPDNQT PDYTYL
GGQRLPGKGW IAPRDLKEML AGDFRTGKIL AQGFGPDNQT PDYTYLKGDI TAAYSAKVKE
*PEPTIDE 2C*

VKRSFLFLNL KDAKVPAAMI VFDKVVASNP DFKKFWLLHS IEQPEIKGNQ ITIKRTKNGD

SGMLVNTALL PDAANSNITS IGGKGKDFWV FGTNYTNDPK PGTDEALERG EWRVETTPKK

AAAEDYYLNV IQIADNTQQK LHEVKRIDGD KVVGVQLADR IVTFSKTSET VDRPFGFSVV

GKGTFKFVMT DLLAGTWQVL KDGKILYPAL SAKGDDGPLY FEGTEGTYRF LR

FIG.5

| | |
|---|---|
| ATGACTACGA AAATTTTTAA AAGGATCATT GTATTTGCTG TAATTGCCCT | 50 |
| ATCGTCGGGA AATATACTTG CACAAAGCTC TTCCATTACC AGGAAAGATT | 100 |
| TTGACCACAT CAACCTTGAG TATTCCGGAC TGGAAAAGGT TAATAAAGCA | 150 |
| GTTGCTGCCG GCAACTATGA CGATGCGGCC AAAGCATTAC TGGCATACTA | 200 |
| CAGGGAAAAA AGTAAGGCCA GGGAACCTGA TTTCAGTAAT GCAGAAAAGC | 250 |
| CTGCCGATAT ACGCCAGCCC ATAGATAAGG TTACGCGTGA AATGGCCGAC | 300 |
| AAGGCTTTGG TCCACCAGTT TCAACCGCAC AAAGGCTACG GCTATTTTGA | 350 |
| TTATGGTAAA GACATCAACT GGCAGATGTG GCCGGTAAAA GACAATGAAG | 400 |
| TACGCTGGCA GTTGCACCGT GTAAAATGGT GGCAGGCTAT GGCCCTGGTT | 450 |
| TATCACGCTA CGGGCGATGA AAAATATGCA AGAGAATGGG TATATCAGTA | 500 |
| CAGCGATTGG GCCAGAAAAA ACCCATTGGG CCTGTCGCAG GATAATGATA | 550 |
| AATTTGTGTG GCGGCCCCTT GAAGTGTCGG ACAGGGTACA AAGTCTTCCC | 600 |
| CCAACCTTCA GCTTATTTGT AAACTCGCCA GCCTTTACCC CAGCCTTTTT | 650 |
| AATGGAATTT TTAAACAGTT ACCACCAACA GGCCGATTAT TTATCTACGC | 700 |
| ATTATGCCGA ACAGGGAAAC CACCGTTTAT TTGAAGCCCA ACGCAACTTG | 750 |
| TTTGCAGGGG TATCTTTCCC TGAATTTAAA GATTCACCAA GATGGAGGCA | 800 |
| AACCGGCATA TCGGTGCTGA ACACCGAGAT CAAAAAACAG GTTTATGCCG | 850 |
| ATGGGATGCA GTTTGAACTT TCACCAATTT ACCATGTAGC TGCCATCGAT | 900 |
| ATCTTCTTAA AGGCCTATGG TTCTGCAAAA CGAGTTAACC TTGAAAAAGA | 950 |
| ATTTCCGCAA TCTTATGTAC AAACTGTAGA AAATATGATT ATGGCGCTGA | 1000 |

FIG.8A

| | |
|---|---:|
| TCAGTATTTC ACTGCCAGAT TATAACACCC CTATGTTTGG AGATTCATGG | 1050 |
| ATTACAGATA AAAATTTCAG GATGGCACAG TTTGCCAGCT GGGCCCGGGT | 1100 |
| TTTCCCGGCA AACCAGGCCA TAAAATATTT TGCTACAGAT GGCAAACAAG | 1150 |
| GTAAGGCGCC TAACTTTTTA TCCAAAGCAT TGAGCAATGC AGGCTTTTAT | 1200 |
| ACGTTTAGAA GCGGATGGGA TAAAAATGCA ACCGTTATGG TATTAAAAGC | 1250 |
| CAGTCCTCCC GGAGAATTTC ATGCCCAGCC GGATAACGGG ACTTTTGAAC | 1300 |
| TTTTTATAAA GGGCAGAAAC TTTACCCCAG ACGCCGGGGT ATTTGTGTAT | 1350 |
| AGCGGCGACG AAGCCATCAT GAAACTGCGG AACTGGTACC GTCAAACCCG | 1400 |
| CATACACAGC ACGCTTACAC TCGACAATCA AAATATGGTC ATTACCAAAG | 1450 |
| CCCGGCAAAA CAAATGGGAA ACAGGAAATA ACCTTGATGT GCTTACCTAT | 1500 |
| ACCAACCCAA GCTATCCGAA TCTGGACCAT CAGCGCAGTG TACTTTTCAT | 1550 |
| CAACAAAAAA TACTTTCTGG TCATCGATAG GGCAATAGGC GAAGCTACCG | 1600 |
| GAAACCTGGG CGTACACTGG CAGCTTAAAG AAGACAGCAA CCCTGTTTTC | 1650 |
| GATAAGACAA AGAACCGGGT TTACACCACT TACACAGATG GTAACAACCT | 1700 |
| GATGATCCAA TCGTTGAATG CGGACAGGAC CAGCCTCAAT GAAGAAGAAG | 1750 |
| GAAAGGTATC TTATGTTTAC AATAAGGAGC TGAAAAGACC TGCTTTCGTA | 1800 |
| TTTGAAAAGC CTAAAAAGAA TGCCGGCACA CAAAATTTTG TCAGTATAGT | 1850 |
| TTATCCATAC GACGGCCAGA AGGCTCCAGA GATCAGCATA CGGGAAAACA | 1900 |
| AGGGCAATGA TTTTGAGAAA GGCAAGCTTA ATCTAACCCT TACCATTAAC | 1950 |
| CGAAAACAAC AGCTTGTGTT GGTTCCTTAG | 1980 |

FIG.8B

```
MTTKIFKRII VFAVIALSSG NILAQSSSIT RKDFDHINLE YSGLEKVNKA VAAGNYDDAA

KALVHMFWPH KGYGYFDYGK
KALLAYYREK SKAREPDFSN AEKPADIRQP IDKVTREMAD KALVHQFQPH KGYGYFDYGK
                                                       PEPTIDE 3C

DIN    LIK -NEVRWQLHR VK
DINWQMWPVK DNEVRWQLHR VKWWQAMALV YHATGDEKYA REWVYQYSDW ARKNPLGLSQ
           PEPTIDE 3A

DNDKFVWRPL EVSDRVQSLP PTFSLFVNSP AFTPAFLMEF LNSYHQQADY LSTHYAEQGN

HRLFEAQRNL FAGVSFPEFK DSPRWRQTGI SVLNTEIKKQ VYADGMQFEL SPIYHVAAID

IFLKAYGSAK RVNLEKEFPQ SYVQTVENMI MALISISLPD YNTPMFGDSW ITDKNFRMAQ

VLKASPP
FASWARVFPA NQAIKYFATD GKQGKAPNFL SKALSNAGFY TFRSGWDKNA TVMVLKASPP

GEFHAQPDNG TFELFI
GEFHAQPDNG TFELFIKGRN FTPDAGVFVY SGDEAIMKLR NWYRQTRIHS TLTLDNQNMV
PEPTIDE 3B

ITKARQNKWE TGNNLDVLTY TNPSYPNLDH QRSVLFINKK YFLVIDRAIG EATGNLGVHW

QLKEDSNPVF DKTKNRVYTT YRDGNNLMIQ SLNADRTSLN EEEGKVSYVY NKELKRPAFV

FEKPKKNAGT QNFVSIVYPY DGQKAPEISI RENKGNDFEK GKLNLTLTIN GKQQLVLVP
```

FIG.9

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 2339 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
ATGAAAAGAC AATTATACCT GTATGTGATT TTTGTTGTAG TTGAACTTAT GGTTTTTACA        60

ACAAAGGGCT ATTCCCAAAC CAAGGCCGAT GTGGTTTGGA AAGACGTGGA TGGCGTATCT       120

ATGCCCATAC CCCCTAAGAC CCACCCGCGT TTGTATCTAC GTGAGCAGCA AGTTCCTGAC       180

CTGAAAAACA GGATGAACGA CCCTAAACTG AAAAAAGTTT GGGCCGATAT GATCAAGATG       240

CAGGAAGACT GGAAGCCAGC TGATATTCCT GAAGTTAAAG ACTTTCGTTT TTATTTTAAC       300

CAGAAAGGGC TTACTGTAAG GGTTGAACTA ATGGCCCTGA ACTATCTGAT GACCAAGGAT       360

CCAAAGGTAG GACGGGAAGC CATCACTTCA ATTATTGATA CCCTTGAAAC TGCAACTTTT       420

AAACCAGCAG GTGATATTTC GAGAGGGATA GTGATATTTC GAGAGGGATA GGCCTGTTTA       480

TGGTTACAGG GGCCATTGTG TATGACTGGT GCTACGATCA GCTGAAACCA GAAGAGAAAA       540
```

```
CACGTTTTGT GAAGGCATTT GTGAGGCTGG CCAAAATGCT CGAATGTGGT TATCCTCCGG      600

TAAAAGACAA GTCTATTGTT GGGCATGCTT CCGAATGGAT GATCATGCGG GACCTGCTTT      660

CTGTAGGGAT TGCCATTTAC GATGAATTCC CTGAGATGTA TAACCTGGCT GCGGGTCGTT      720

TTTTCAAAGA ACACCTGGTT GCCCGCAACT GGTTTTATCC CTCGCATAAC TACCATCAGG      780

GTATGTCATA CCTGAACGTA AGATTTACCA ACGACCTTTT TGCCCTCTGG ATATTAGACC      840

GGATGGGCGC TGGTAATGTG TTTAATCCAG GGCAGCAGTT TATCCTTTAT GACGCGATCT      900

ATAAACGCCG CCCCGATGGA CAGATTTTAG CAGGTGGAGA TGTAGATTAT TCCAGGAAAA      960

AACCAAAATA TTATACGATG CCTGCATTGC TTGCAGGTAG CTATTATAAA GATGAATACC     1020

TTAATTACGA ATTCCTGAAA GATCCCAATG TTGAGCCACA TTGCAAATTG TTCGAATTTT     1080

TATGGCGCGA TACCCAGTTG GGAAGTCGTA AGCCTGATGA TTTGCCACTT TCCAGGTACT     1140

CAGGATCGCC TTTTGGATGG ATGATTGCCC GTACCGGATG GGGTCCGGAA AGTGTGATTG     1200

CAGAGATGAA AGTCAACGAA TATTCCTTTC TTAACCATCA GCATCAGGAT GCAGGAGCCT     1260

TCCAGATCTA TTACAAAGGC CCGCTGGCCA TAGATGCAGG CTCGTATACA GGTTCTTCAG     1320

GAGGTTATAA CAGTCCGCAC AACAAGAACT TTTTTAAGCG GACTATTGCA CACAATAGCT     1380

TGCTGATTTA CGATCCTAAA GAAACTTTCA GTTCGTCGGG ATATGGTGGA AGTGACCATA     1440

CCGATTTTGC TGCCAACGAT GGTGGTCAGC GGCTGCCCGG AAAAGGTTGG ATTGCACCCC     1500

GCGACCTTAA AGAAATGCTG GCAGGCGATT TCAGGACCGG CAAAATTCTT GCCCAGGGCT     1560

TTGGTCCGGA TAACCAAACC CCTGATTATA CTTATCTGAA AGGAGACATT ACAGCAGCTT     1620

ATTCGGCAAA AGTGAAGGAA GTAAAACGTT CATTTCTATT CCTGAACCTT AAGGATGCCA     1680

AAGTTCCGGC AGCGATGATC GTTTTTGACA AGGTAGTTGC TTCCAATCCT GATTTTAAGA     1740

AGTTCTGGTT GTTGCACAGT ATTGAGCAGC CTGAAATAAA GGGGAATCAG ATTACCATAA     1800

AACGTACAAA AAACGGTGAT AGTGGGATGT TGGTGAATAC GGCTTTGCTG CCGGATGCGG     1860

CCAATTCAAA CATTACCTCC ATTGGCGGCA AGGGCAAAGA CTTCTGGGTG TTTGGTACCA     1920

ATTATACCAA TGATCCTAAA CCGGGCACGG ATGAAGCATT GGAACGTGGA GAATGGCGTG     1980

TGGAAATCAC TCCAAAAAAG GCAGCAGCCG AAGATTACTA CCTGAATGTG ATACAGATTG     2040

CCGACAATAC ACAGCAAAAA TTACACGAGG TGAAGCGTAT TGACGGTGAC AAGGTTGTTG     2100

GTGTGCAGCT TGCTGACAGG ATAGTTACTT TTAGCAAAAC TTCAGAAACT GTTGATCGTC     2160

CCTTTGGCTT TTCCGTTGTT GGTAAAGGAA CATTCAAATT TGTGATGACC GATCTTTTAG     2220

CGGGTACCTG GCAGGTGCTG AAAGACGGAA AAATACTTTA TCCTGCGCTT TCTGCAAAAG     2280

GTGATGATGG ACCCCTTTAT TTTGAAGGAA CTGAAGGAAC CTACCGTTTT TTGAGATAA      2339
```

(2) INFORMATION FOR SEQ ID NO:2:

(i) SEQUENCE CHARACTERISTICS:
        (A) LENGTH: 772 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Arg Gln Leu Tyr Leu Tyr Val Ile Phe Val Val Glu Leu
 1               5                  10                  15

Met Val Phe Thr Thr Lys Gly Tyr Ser Gln Thr Lys Ala Asp Val Val
            20                  25                  30

Trp Lys Asp Val Asp Gly Val Ser Met Pro Ile Pro Pro Lys Thr His
```

```
                35                  40                  45
    Pro Arg Leu Tyr Leu Arg Glu Gln Gln Val Pro Asp Leu Lys Asn Arg
        50                  55                  60

Met Asn Asp Pro Lys Leu Lys Lys Val Trp Ala Asp Met Ile Lys Met
    65                  70                  75                  80

Gln Glu Asp Trp Lys Pro Ala Asp Ile Pro Glu Val Lys Asp Phe Arg
                    85                  90                  95

Phe Tyr Phe Asn Gln Lys Gly Leu Thr Val Arg Val Glu Leu Met Ala
                    100                 105                 110

Leu Asn Tyr Leu Met Thr Lys Asp Pro Lys Val Gly Arg Glu Ala Ile
                115                 120                 125

Thr Ser Ile Ile Asp Thr Leu Glu Thr Ala Thr Phe Lys Pro Ala Gly
    130                 135                 140

Asp Ile Ser Arg Gly Ile Gly Leu Phe Met Val Thr Gly Ala Ile Val
    145                 150                 155                 160

Tyr Asp Trp Cys Tyr Asp Gln Leu Lys Pro Glu Lys Thr Arg Phe
                    165                 170                 175

Val Lys Ala Phe Val Arg Leu Ala Lys Met Leu Glu Cys Gly Tyr Pro
                    180                 185                 190

Pro Val Lys Asp Lys Ser Ile Val Gly His Ala Ser Glu Trp Met Ile
                    195                 200                 205

Met Arg Asp Leu Leu Ser Val Gly Ile Ala Ile Tyr Asp Glu Phe Pro
    210                 215                 220

Glu Met Tyr Asn Leu Ala Ala Gly Arg Phe Phe Lys Glu His Leu Val
    225                 230                 235                 240

Ala Arg Asn Trp Phe Tyr Pro Ser His Asn Tyr His Gln Gly Met Ser
                    245                 250                 255

Tyr Leu Asn Val Arg Phe Thr Asn Asp Leu Phe Ala Leu Trp Ile Leu
                    260                 265                 270

Asp Arg Met Gly Ala Gly Asn Val Phe Asn Pro Gly Gln Gln Phe Ile
                275                 280                 285

Leu Tyr Asp Ala Ile Tyr Lys Arg Arg Pro Asp Gly Gln Ile Leu Ala
                290                 295                 300

Gly Gly Asp Val Asp Tyr Ser Arg Lys Lys Pro Lys Tyr Tyr Thr Met
    305                 310                 315                 320

Pro Ala Leu Leu Ala Gly Ser Tyr Lys Asp Glu Tyr Leu Asn Tyr
                    325                 330                 335

Glu Phe Leu Lys Asp Pro Asn Val Glu Pro His Cys Lys Leu Phe Glu
                    340                 345                 350

Phe Leu Trp Arg Asp Thr Gln Leu Gly Ser Arg Lys Pro Asp Asp Leu
                    355                 360                 365

Pro Leu Ser Arg Tyr Ser Gly Ser Pro Phe Gly Trp Met Ile Ala Arg
                370                 375                 380

Thr Gly Trp Gly Pro Glu Ser Val Ile Ala Glu Met Lys Val Asn Glu
    385                 390                 395                 400

Tyr Ser Phe Leu Asn His Gln His Gln Asp Ala Gly Ala Phe Gln Ile
                    405                 410                 415

Tyr Tyr Lys Gly Pro Leu Ala Ile Asp Ala Gly Ser Tyr Thr Gly Ser
                    420                 425                 430

Ser Gly Gly Tyr Asn Ser Pro His Asn Lys Asn Phe Phe Lys Arg Thr
                435                 440                 445

Ile Ala His Asn Ser Leu Leu Ile Tyr Asp Pro Lys Glu Thr Phe Ser
                450                 455                 460
```

```
            Ser Ser Gly Tyr Gly Gly Ser Asp His Thr Asp Phe Ala Ala Asn Asp
            465                 470                 475                 480

Gly Gly Gln Arg Leu Pro Gly Lys Gly Trp Ile Ala Pro Arg Asp Leu
                            485                 490                 495

Lys Glu Met Leu Ala Gly Asp Phe Arg Thr Gly Lys Ile Leu Ala Gln
                        500                 505                 510

Gly Phe Gly Pro Asp Asn Gln Thr Pro Asp Tyr Thr Tyr Leu Lys Gly
                    515                 520                 525

Asp Ile Thr Ala Ala Tyr Ser Ala Lys Val Lys Glu Val Lys Arg Ser
            530                 535                 540

Phe Leu Phe Leu Asn Leu Lys Asp Ala Lys Val Pro Ala Ala Met Ile
            545                 550                 555                 560

Val Phe Asp Lys Val Ala Ser Asn Pro Asp Phe Lys Lys Phe Trp
                            565                 570                 575

Leu Leu His Ser Ile Glu Gln Pro Glu Ile Lys Gly Asn Gln Ile Thr
                        580                 585                 590

Ile Lys Arg Thr Lys Asn Gly Asp Ser Gly Met Leu Val Asn Thr Ala
                    595                 600                 605

Leu Leu Pro Asp Ala Ala Asn Ser Asn Ile Thr Ser Ile Gly Gly Lys
            610                 615                 620

Gly Lys Asp Phe Trp Val Phe Gly Thr Asn Tyr Thr Asn Asp Pro Lys
            625                 630                 635                 640

Pro Gly Thr Asp Glu Ala Leu Glu Arg Gly Glu Trp Arg Val Glu Ile
                            645                 650                 655

Thr Pro Lys Lys Ala Ala Ala Glu Asp Tyr Tyr Leu Asn Val Ile Gln
                        660                 665                 670

Ile Ala Asp Asn Thr Gln Gln Lys Leu His Glu Val Lys Arg Ile Asp
                    675                 680                 685

Gly Asp Lys Val Val Gly Val Gln Leu Ala Asp Arg Ile Val Thr Phe
            690                 695                 700

Ser Lys Thr Ser Glu Thr Val Asp Arg Pro Phe Gly Phe Ser Val Val
            705                 710                 715                 720

Gly Lys Gly Thr Phe Lys Phe Val Met Thr Asp Leu Leu Ala Gly Ile
                            725                 730                 735

Trp Gln Val Leu Lys Asp Gly Lys Ile Leu Tyr Pro Ala Leu Ser Ala
                        740                 745                 750

Lys Gly Asp Asp Gly Pro Leu Tyr Phe Glu Gly Thr Glu Gly Thr Tyr
                    755                 760                 765

Arg Phe Leu Arg
                770

(2) INFORMATION FOR SEQ ID NO:3:

(i) SEQUENCE CHARACTERISTICS:
        (A) LENGTH: 1980 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

ATGACTACGA AAATTTTTAA AAGGATCATT GTATTTGCTG TAATTGCCCT              50

ATCGTCGGGA AATATACTTG CACAAAGCTC TTCCATTACC AGGAAAGATT             100

TTGACCACAT CAACCTTGAG TATTCCGGAC TGGAAAAGGT TAATAAAGCA             150

GTTGCTGCCG GCAACTATGA CGATGCGGCC AAAGCATTAC TGGCATACTA             200
```

```
CAGGGAAAAA AGTAAGGCCA GGGAACCTGA TTTCAGTAAT GCAGAAAAGC      250

CTGCCGATAT ACGCCAGCCC ATAGATAAGG TTACGCGTGA AATGGCCGAC      300

AAGGCTTTGG TCCACCAGTT TCAACCGCAC AAAGGCTACG GCTATTTTGA      350

TTATGGTAAA GACATCAACT GGCAGATGTG CCGGTAAAA GACAATGAAG       400

TACGCTGGCA GTTGCACCGT GTAAAATGGT GGCAGGCTAT GGCCCTGGTT      450

TATCACGCTA CGGGCGATGA AAAATATGCA AGAGAATGGG TATATCAGTA      500

CAGCGATTGG GCCAGAAAAA ACCCATTGGG CCTGTCGCAG GATAATGATA      550

AATTTGTGTG GCGGCCCCTT GAAGTGTCGG ACAGGGTACA AAGTCTTCCC      600

CCAACCTTCA GCTTATTTGT AAACTCGCCA GCCTTTACCC CAGCCTTTTT      650

AATGGAATTT TAAACAGTT ACCACCAACA GGCCGATTAT TTATCTACGC       700

ATTATGCCGA ACAGGGAAAC CACCGTTTAT TTGAAGCCCA ACGCAACTTG      750

TTTGCAGGGG TATCTTTCCC TGAATTTAAA GATTCACCAA GATGGAGGCA      800

AACCGGCATA TCGGTGCTGA ACACCGAGAT CAAAAAACAG GTTTATGCCG      850

ATGGGATGCA GTTTGAACTT TCACCAATTT ACCATGTAGC TGCCATCGAT      900

ATCTTCTTAA AGGCCTATGG TTCTGCAAAA CGAGTTAACC TTGAAAAAGA      950

ATTTCCGCAA TCTTATGTAC AAACTGTAGA AAATATGATT ATGGCGCTGA     1000

TCAGTATTTC ACTGCCAGAT TATAACACCC CTATGTTTGG AGATTCATGG     1050

ATTACAGATA AAAATTTCAG GATGGCACAG TTTGCCAGCT GGGCCCGGGT     1100

TTTCCCGGCA AACCAGGCCA TAAATATTT TGCTACAGAT GGCAAACAAG      1150

GTAAGGCGCC TAACTTTTTA TCCAAAGCAT TGAGCAATGC AGGCTTTTAT     1200

ACGTTTAGAA GCGGATGGGA TAAAAATGCA ACCGTTATGG TATTAAAAGC     1250

CAGTCCTCCC GGGGAATTTC ATGCCCAGCC GGATAACGGG ACTTTTGAAC     1300

TTTTTATAAA GGGCAGAAAC TTTACCCCAG ACGCCGGGGT ATTTGTGTAT     1350

AGCGGCGACG AAGCCATCAT GAAACTGCGG AACTGGTACC GTCAAACCCG     1400

CATACACAGC ACGCTTACAC TCGACAATCA AAATATGGTC ATTACCAAAG     1450

CCCGGCAAAA CAAATGGGAA ACAGGAAATA ACCTTGATGT GCTTACCTAT     1500

ACCAACCCAA GCTATCCGAA TCTGGACCAT CAGCGCAGTG TACTTTTCAT     1550

CAACAAAAAA TACTTTCTGG TCATCGATAG GGCAATAGGC GAAGCTACCG     1600

GAAACCTGGG CGTACACTGG CAGCTTAAAG AAGACAGCAA CCCTGTTTTC     1650

GATAAGACAA AGAACCGGGT TTACACCACT TACAGAGATG GTAACAACCT     1700

GATGATCCAA TCGTTGAATG CGGACAGGAC CAGCCTCAAT GAAGAAGAAG     1750

GAAAGGTATC TTATGTTTAC AATAAGGAGC TGAAAAGACC TGCTTTCGTA     1800

TTTGAAAAGC CTAAAAAGAA TGCCGGCACA CAAAATTTTG TCAGTATAGT     1850

TTATCCATAC GACGGCCAGA AGGCTCCAGA GATCAGCATA CGGGAAAACA     1900

AGGGCAATGA TTTTGAGAAA GGCAAGCTTA ATCTAACCCT TACCATTAAC     1950

GGAAAACAAC AGCTTGTGTT GGTTCCTTAG                           1980
```

(2) INFORMATION FOR SEQ ID NO:4:

(i) SEQUENCE CHARACTERISTICS:
        (A) LENGTH: 659 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Thr Lys Ile Phe Lys Arg Ile Ile Val Phe Ala Val Ile Ala
 1               5                  10                  15

Leu Ser Ser Gly Asn Ile Leu Ala Gln Ser Ser Ile Thr Arg Lys
                20                  25                  30

Asp Phe Asp His Ile Asn Leu Glu Tyr Ser Gly Leu Glu Lys Val Asn
                35                  40                  45

Lys Ala Val Ala Ala Gly Asn Tyr Asp Asp Ala Lys Ala Leu Leu
 50                  55                  60

Ala Tyr Tyr Arg Glu Lys Ser Lys Ala Arg Glu Pro Asp Phe Ser Asn
 65                  70                  75                  80

Ala Glu Lys Pro Ala Asp Ile Arg Gln Pro Ile Asp Lys Val Thr Arg
                85                  90                  95

Glu Met Ala Asp Lys Ala Leu Val His Gln Phe Gln Pro His Lys Gly
                100                 105                 110

Tyr Gly Tyr Phe Asp Tyr Gly Lys Asp Ile Asn Trp Gln Met Trp Pro
                115                 120                 125

Val Lys Asp Asn Glu Val Arg Trp Gln Leu His Arg Val Lys Trp Trp
 130                 135                 140

Gln Ala Met Ala Leu Val Tyr His Ala Thr Gly Asp Glu Lys Tyr Ala
145                 150                 155                 160

Arg Glu Trp Val Tyr Gln Tyr Ser Asp Trp Ala Arg Lys Asn Pro Leu
                165                 170                 175

Gly Leu Ser Gln Asp Asn Asp Lys Phe Val Trp Arg Pro Leu Glu Val
                180                 185                 190

Ser Asp Arg Val Gln Ser Leu Pro Pro Thr Phe Ser Leu Phe Val Asn
                195                 200                 205

Ser Pro Ala Phe Thr Pro Ala Phe Leu Met Glu Phe Leu Asn Ser Tyr
 210                 215                 220

His Gln Gln Ala Asp Tyr Leu Ser Thr His Tyr Ala Glu Gln Gly Asn
225                 230                 235                 240

His Arg Leu Phe Glu Ala Gln Arg Asn Leu Phe Ala Gly Val Ser Phe
                245                 250                 255

Pro Glu Phe Lys Asp Ser Pro Arg Trp Arg Gln Thr Gly Ile Ser Val
                260                 265                 270

Leu Asn Thr Glu Ile Lys Lys Gln Val Tyr Ala Asp Gly Met Gln Phe
                275                 280                 285

Glu Leu Ser Pro Ile Tyr His Val Ala Ala Ile Asp Ile Phe Leu Lys
                290                 295                 300

Ala Tyr Gly Ser Ala Lys Arg Val Asn Leu Glu Lys Glu Phe Pro Gln
305                 310                 315                 320

Ser Tyr Val Gln Thr Val Glu Asn Met Ile Met Ala Leu Ile Ser Ile
                325                 330                 335

Ser Leu Pro Asp Tyr Asn Thr Pro Met Phe Gly Asp Ser Trp Ile Thr
                340                 345                 350

Asp Lys Asn Phe Arg Met Ala Gln Phe Ala Ser Trp Ala Arg Val Phe
                355                 360                 365

Pro Ala Asn Gln Ala Ile Lys Tyr Phe Ala Thr Asp Gly Lys Gln Gly
                370                 375                 380

Lys Ala Pro Asn Phe Leu Ser Lys Ala Leu Ser Asn Ala Gly Phe Tyr
385                 390                 395                 400
```

```
            Thr Phe Arg Ser Gly Trp Asp Lys Asn Ala Thr Val Met Val Leu Lys
                        405                 410                 415

Ala Ser Pro Pro Gly Glu Phe His Ala Gln Pro Asp Asn Gly Thr Phe
                        420                 425                 430

Glu Leu Phe Ile Lys Gly Arg Asn Phe Thr Pro Asp Ala Gly Val Phe
                        435                 440                 445

Val Tyr Ser Gly Asp Glu Ala Ile Met Lys Leu Arg Asn Trp Tyr Arg
                        450                 455                 460

Gln Thr Arg Ile His Ser Thr Leu Thr Leu Asp Asn Gln Asn Met Val
            465                 470                 475                 480

Ile Thr Lys Ala Arg Gln Asn Lys Trp Glu Thr Gly Asn Asn Leu Asp
                        485                 490                 495

Val Leu Thr Tyr Thr Asn Pro Ser Tyr Pro Asn Leu Asp His Gln Arg
                        500                 505                 510

Ser Val Leu Phe Ile Asn Lys Lys Tyr Phe Leu Val Ile Asp Arg Ala
                        515                 520                 525

Ile Gly Glu Ala Thr Gly Asn Leu Gly Val His Trp Gln Leu Lys Glu
                        530                 535                 540

Asp Ser Asn Pro Val Phe Asp Lys Thr Lys Asn Arg Val Tyr Thr Thr
            545                 550                 555                 560

Tyr Arg Asp Gly Asn Asn Leu Met Ile Gln Ser Leu Asn Ala Asp Arg
                        565                 570                 575

Thr Ser Leu Asn Glu Glu Glu Gly Lys Val Ser Tyr Val Tyr Asn Lys
                        580                 585                 590

Glu Leu Lys Arg Pro Ala Phe Val Phe Glu Lys Pro Lys Lys Asn Ala
                        595                 600                 605

Gly Thr Gln Asn Phe Val Ser Ile Val Tyr Pro Tyr Asp Gly Gln Lys
                        610                 615                 620

Ala Pro Glu Ile Ser Ile Arg Glu Asn Lys Gly Asn Asp Phe Glu Lys
            625                 630                 635                 640

Gly Lys Leu Asn Leu Thr Leu Thr Ile Asn Gly Lys Gln Gln Leu Val
                        645                 650                 655

Leu Val Pro (2) INFORMATION FOR SEQ ID NO:5:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:5:

Glu Phe Pro Glu Met Tyr Asn Leu Ala Ala Gly Arg
    1               5                   10

(2) INFORMATION FOR SEQ ID NO:6:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:6:

Lys Pro Ala Asp Ile Pro Glu Val Lys Asp Gly Arg
    1               5                   10
```

(2) INFORMATION FOR SEQ ID NO:7:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:7:

Leu Ala Gly Asp Phe Val Thr Gly Lys Ile Leu Ala Gln Gly Phe Gly
    1               5                   10                  15

Pro Asp Asn Gln Thr Pro Asp Tyr Thr Tyr Leu
                20                  25

(2) INFORMATION FOR SEQ ID NO:8:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO:8:

Leu Ile Lys Asn Glu Val Arg Trp Gln Leu His Arg Val Lys
    1               5                   10

(2) INFORMATION FOR SEQ ID NO:9:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:9:

Val Leu Lys Ala Ser Pro Pro Gly Glu Phe His Ala Gln Pro Asp Asn
    1               5                   10                  15

Gly Thr Phe Glu Leu Phe Ile
                20

(2) INFORMATION FOR SEQ ID NO:10:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (xi) SEQUENCE DESCRIPTION: SEQ ID NO:10:

Lys Ala Leu Val His Trp Phe Trp Pro His Lys Gly Tyr Gly Tyr Phe
    1               5                   10                  15

Asp Tyr Gly Lys Asp Ile Asn
                20

(2) INFORMATION FOR SEQ ID NO:11:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

```
        (xi) SEQUENCE DESCRIPTION: SEQ ID NO:11:

GAATTCCCTG AGATGTACAA TCTGGCCGC                                              29

(2) INFORMATION FOR SEQ ID NO:12:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:12:

CCGGCAGCCA GATTGTACAT TTCAGG                                                 26

(2) INFORMATION FOR SEQ ID NO:13:

(i) SEQUENCE CHARACTERISTICS:
            (A) LENGTH: 29 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:13:

AAACCCGCCG ACATTCCCGA AGTAAAAGA                                              29

(2) INFORMATION FOR SEQ ID NO:14:

(i) SEQUENCE CHARACTERISTICS:
            (A) LENGTH: 29 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:14:

CGAAAGTCTT TTACTTCGGG AATGTCGGC                                              29

(2) INFORMATION FOR SEQ ID NO:15:

(i) SEQUENCE CHARACTERISTICS:
            (A) LENGTH: 38 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:15:

TGAGGATTCA TGCAAACCAA GGCCGATGTG GTTTGGAA                                    38

(2) INFORMATION FOR SEQ ID NO:16:

(i) SEQUENCE CHARACTERISTICS:
            (A) LENGTH: 24 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:16:

GGAGGATAAC CACATTCGAG CATT                                                   24
```

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

GAATTCCATC AGTTTCAGCC GCATAAA                                          27

(2) INFORMATION FOR SEQ ID NO:18:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

GAATTCTTTA TGCGGCTGAA ACTGATG                                          27

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

GAATTCCCGC CGGGCGAATT TCATGC                                           26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:20:

GAATTCGCAT GAAATTCGCC CGGCGG                                           26

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:21:

GGGAATTTCC ATGCCCAGCC GAAATGGAC                                      29

(2) INFORMATION FOR SEQ ID NO:22:

(i) SEQUENCE CHARACTERISTICS:
        (A) LENGTH: 28 base pairs
        (B) TYPE: nucleic acid -continued

```
        (C) STRANDEDNESS: double
        (D) TOPOLOGY: linear (ii) MOLECULE TYPE: DNA (genomic)

(xi) SEQUENCE DESCRIPTION: SEQ ID NO:22:

GTCCATTTCG GCTGGGCATG AAATTCCC                                      28

(2) INFORMATION FOR SEQ ID NO:23:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:23:

GTCATCAGTT CAGCCCATAA AGGTATGG                                      28

(2) INFORMATION FOR SEQ ID NO:24:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:24:

CCCATACCTT ATGGGCTGAA CTGATGAC                                      28

(2) INFORMATION FOR SEQ ID NO:25:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:25:

CGCGGATCCA TGCAAAGCTC TTCCATT                                       27

(2) INFORMATION FOR SEQ ID NO:26:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:26:

CGCGGATCCT CAAAGCTTGC CTTTCTC                                       27
```

NUCLEIC ACID SEQUENCES AND EXPRESSION SYSTEMS FOR HEPARINASE II AND HEPARINASE III DERIVED FROM *FLAVOBACTERIUM HEPARINUM*

This application is a division of application Ser. No. 08/258,639, filed Jun. 10, 1994, now U.S. Pat. No. 5,681,733.

BACKGROUND OF THE INVENTION

This invention is directed to cloning, sequencing and expressing heparinase II and heparinase III from *Flavobacterium heparinum*.

The heparin and heparan sulfate family of molecules is comprised of glycosaminoglycans of repeating glucosamine and hexuronic acid residues, either iduronic or glucuronic, in which the 2, 3 or 6 position of glucosamine or the 2 position of the hexuronic acid may be sulfated. Variations in the extent and location of sulfation as well as conformation of the alternating hexuronic acid residue leads to a high degree of heterogeneity of the molecules within this family. Conventionally, heparin refers to molecules which possess a high sulfate content, 2.6 sulfates per disaccharide, and a higher amount of iduronic acid. Conversely, heparan sulfate contains lower amounts of sulfate, 0.7 to 1.3 sulfates per disaccharide, and less iduronic acid. However, variants of intermediate composition exist and heparins from all biological sources have not yet been characterized.

Specific sulfation/glycosylation patterns of heparin have been associated with biological function, such as the antithrombin binding site described by Choay et al., *Thrombosis Res.* 18: 573–578 (1980), and the fibroblast growth factor binding site described by Turnbull et al., *J. Biol. Chem.* 267: 10337–10341 (1992). It is apparent from these examples that heparin's interaction with certain molecules results from the conformation imparted by specific sequences and not solely due to electrostatic interactions imparted by its high sulfate composition. Heparin interacts with a variety of mammalian molecules, thereby modulating several biological events such as hemostasis, cell proliferation, migration and adhesion as summarized by Kjellen and Lindahl, *Ann Rev Biochem* 60: 443–475 (1991) and Burgess and Macaig, *Ann. Rev. Biochem.* 58: 575–606 (1989). Heparin, extracted from bovine lungs and porcine intestines, has been used as an anticoagulant since its antithrombotic properties were discovered by McLean, *Am. J. Physiol.* 41: 250–257 (1916). Heparin and chemically modified heparins are continually under review for medical applications in the areas of wound healing and treating vascular disease.

Heparin degrading enzymes, referred to as heparinases or heparin lyases, have been identified in several microorganisms including: *Flavobacterium heparinum*, Bacteriodes sp. and *Aspergillus nidulans* as summarized by Linhardt et al., *Appl. Biochem. Biotechnol.* 12: 135–177 (1986). Heparan sulfate degrading enzymes, referred to as heparitinases or heparan sulfate lyases, have been detected in platelets (Oldberg et al., *Biochemistry* 19: 5755–5762 (1980)), tumor (Nakajima et al., *J. Biol. Chem.* 259: 2283–2290 (1984)) and endothelial cells (Gaal et al., *Biochem. Biophys. Res. Comm.* 161: 604–614 (1989)). Mammalian heparanases catalyze the hydrolysis of the carbohydrate backbone of heparan sulfate at the hexuronic acid (1→4) glucosamine linkage (Nakajima et al., *J. Cell. Biochem.* 36: 157–167 (1988)) and are inhibited by the highly sulfated heparin. However, accurate biochemical characterizations of these enzymes has thus far been prevented by the lack of a method to obtain homogeneous preparations of the molecules.

*Flavobacterium heparinum* produces heparin and heparan sulfate degrading enzymes termed heparinase I (E.C. 4.2.2.7) as described by Yang et al., *J. Biol. Chem.* 260(3): 1849–1857 (1985), heparinase II as described by Zimmermann and Cooney, U.S. Pat. No. 5,169,772, and heparinase III (E.C. 4.2.2.8) as described by Lohse and Linhardt, *J. Biol. Chem.* 267: 24347– 24355 (1992). These enzymes catalyze an eliminative cleavage of the (α1→4) carbohydrate bond between glucosamine and hexuronic acid residues in the heparin/heparan sulfate backbone. The three enzyme variants differ in their action on specific carbohydrate residues. Heparinase I cleaves at α-D-GlcNp2S6S (1→4 4)α-L-IdoAp2S, heparinase III at α-D-GlcNp2Ac (or2S)60H(1→4 4)β-D-GlcAp and heparinase II at either linkage as described by Desai et al., *Arch. Biochem. Biophys.* 306(2): 461–468 (1993). Secondary cleavage sites for each enzyme also have been described by Desai et al.

Heparinase I has been used clinically to neutralize the anticoagulant properties of heparin as summarized by Waugh and Zimmermann, *Perfusion Rev.* 1(2): 8–13, 1993. Heparinase I and III have been shown to modulate cell-growth factor interactions as demonstrated by Bashkin et al., *J. Cell Physiol.* 151:126–137 (1992) and cell-lipoprotein interactions as demonstrated by Chappell et al., *J. Biol. Chem.* 268(19):14168–14175 (1993). The availability of heparin degrading enzymes of sufficient purity and quantity could lead to the development of important diagnostic and therapeutic formulations.

SUMMARY OF THE INVENTION

Prior to the present invention, partially purified heparinases II and III were available, but their amino acid sequences were unknown. Cloning these enzymes was difficult because of toxicity to the host cells. The present inventors were able to clone the genes for heparinases II and III, and herein provide their nucleotide and amino acid sequences.

A method is described for the isolation of highly purified heparin and heparan sulfate degrading enzymes from *F. heparinum*.

Characterization of each protein demonstrated that heparinases I, II and III are glycoproteins. All three proteins are modified at their N-terminal amino acid residue. Antibodies generated by injecting purified heparinases into rabbits yielded anti-sera which demonstrated a high degree of cross reactivity to proteins from *F. heparinum*. Polyclonal antibodies were separated by affinity chromatography into fractions which bind the amino acid portion of the proteins and a fraction which binds the post-translational modification allowing for the use of these antibodies to specifically distinguish the native and recombinant forms of each heparinase protein.

Amino acid sequence information was used to synthesize oligonucleotides that were subsequently used in a polymerase chain reaction (PCR) to amplify a portion of the heparinase II and heparinase III genes. Amplified regions were used in an attempt to identify clones from a λDASH-II gene library which contained *F. heparinum* genomic DNA. Natural selection against clones containing the entire heparinase II and III genes was observed. This was circumvented by cloning sections of the heparinase II gene separately, and by screening host strains for stable maintenance of complete heparinase III clones. Expression of heparinase II and III was achieved by use of a vector containing a modified ribosome binding site which was shown to increase the expression of heparinase I to significant levels.

This patent describes the gene and amino acid sequences for heparinase II and III from *F. heparinum*, which may be used in conjunction with suitable expression systems to produce the enzymes. Also described, is a modified ribosome binding sequence used to express heparinase I, II, and III.

BRIEF DESCRIPTION OF THE DRAWINGS

FIG. 1 shows the modifications to the tac promoter ribosome binding region, which were evaluated for the level of expression of heparinase I. The original sequence, as found in pBhep, and the modified sequences, as found in pGhep and pΔ4hep, are shown with the Shine-Dalgarno sequences (S-D) and the heparinase I gene start codon, underlined. The gap (in nucleotides, nt) between these regions is indicated below each sequence. The ribosome binding region for pGB contains no start codon, and has a BamHI site (underlined) in place of the EcoRI site (GAATTC) found in pGhep.

FIG. 4 shows the nucleic acid sequence for the heparinase II gene from *Flavobacterium heparinum* (SEQU ID NO:1).

FIG. 5 shows the amino acid sequence for heparinase II from *Flavobacterium heparinum* (SEQU ID NO:2). The leader peptide sequence is underlined. The mature protein starts at Q-26. Peptides 2A, 2B and 2C are indicated at their corresponding positions within the protein.

FIG. 8 shows the nucleic acid sequence for the heparinase III gene from *Flavobacterium heparinum* (SEQU ID NO:3).

FIG. 9 shows the amino acid sequence for heparinase III from *Flavobacterium heparinum* (SEQU ID NO:4). The leader peptide sequence is underlined. The mature protein starts at Q-25. Peptides 3A, 3B and 3C are indicated at their corresponding positions within the protein.

DETAILED DESCRIPTION OF THE INVENTION

Figure 2:
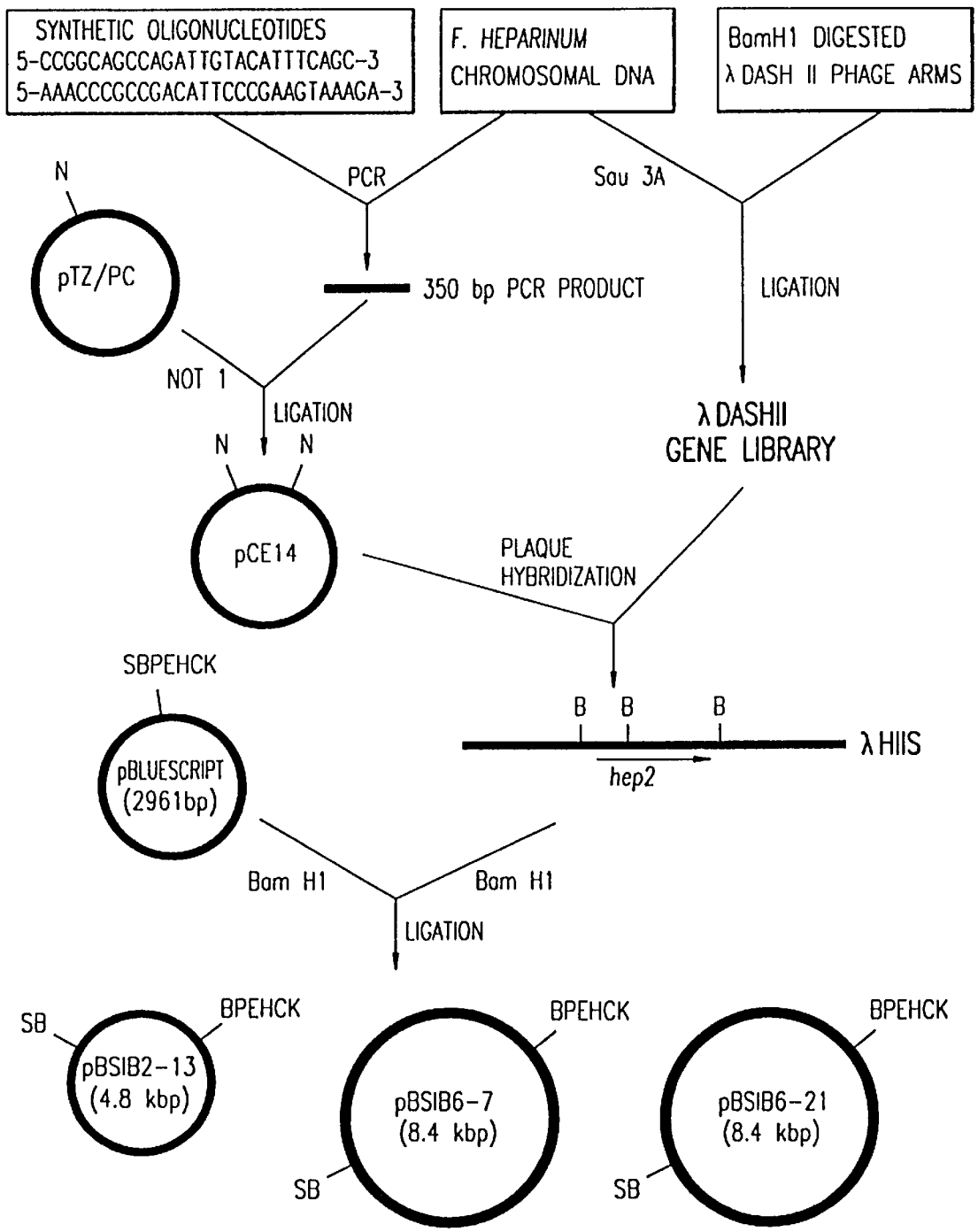
FIG. 2 shows the construction of plasmids used to sequence the heparinase II gene from *Flavobacterium heparinum*. Restriction sites are: N=NotI, Nc=NcoI, S=SalI, B=BamHI, P=PstI, E=EcoRI, H=HindIII, C=ClaI and K=KpnI.

To aid in the understanding of the specification and claims, including the scope to be given such terms, the following definitions are provided.

Gene. By the term "gene" is intended a DNA sequence which encodes through its template or messenger RNA a sequence of amino acids characteristic of a specific peptide. Further, the term includes intervening, non-coding regions, as well as regulatory regions, and can include 5' and 3' ends.

Gene sequence. The term "gene sequence" is intended to refer generally to a DNA molecule which contains one or more genes, or gene fragments, as well as a DNA molecule which contains a non-transcribed or non-translated sequence. The term is further intended to include any combination of gene(s), gene fragments(s), non-transcribed sequence(s) or non-translated sequence(s) which are present on the same DNA molecule.

The present sequences may be derived from a variety of sources including DNA, synthetic DNA, RNA, or combinations thereof. Such gene sequences may comprise genomic DNA which may or may not include naturally occurring introns. Moreover, such genomic DNA may be obtained in association with promoter regions or poly A sequences. The gene sequences, genomic DNA or cDNA may be obtained in any of several ways. Genomic DNA can be extracted and purified from suitable cells, such as brain cells, by means well known in the art. Alternatively, mRNA can be isolated from a cell and used to produce cDNA by reverse transcription or other means.

Recombinant DNA. By the term "recombinant DNA" is meant a molecule that has been recombined by in vitro splicing cDNA or a genomic DNA sequence.

Cloning Vehicle. A plasmid or phage DNA or other DNA sequence which is able to replicate in a host cell. The cloning vehicle is characterized by one or more endonuclease recognition sites at which is DNA sequences may be cut in a determinable fashion without loss of an essential biological function of the DNA, which may contain a marker suitable for use in the identification of transformed cells. Markers include for example, tetracycline resistance or ampicillin resistance. The word vector can be used to connote a cloning vehicle.

Expression Control Sequence. A sequence of nucleotides that controls or regulates expression of structural genes when operably linked to those genes. They include the lac systems, the trp system major operator and promoter regions of the phage lambda, the control region of fd coat protein and other sequences known to control the expression of genes in prokaryotic or eukaryotic cells.

Expression vehicle, A vehicle or vector similar to a cloning vehicle but which is capable of expressing a gene which has been cloned into it, after transformation into a host. The cloned gene is usually placed under the control of (i.e., operable linked to) certain control sequences such as promoter sequences. Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Promoter. The term "promoter" is intended to refer to a DNA sequence which can be recognized by an RNA polymerase. The presence of such a sequence permits the RNA polymerase to bind and initiate transcription of operably linked gene sequences.

Promoter region. The term "promoter region" is intended to broadly include both the promoter sequence as well as gene sequences which may be necessary for the initiation of transcription. The presence of a promoter region is, therefore, sufficient to cause the expression of an operably linked gene sequence.

Operably Linked. As used herein, the term "operably linked" means that the promoter controls the initiation of expression of the gene. A promoter is operably linked to a sequence of proximal DNA if upon introduction into a host cell the promoter determines the transcription of the proximal DNA sequence or sequences into one or more species of RNA. A promoter is operably linked to a DNA sequence if the promoter is capable if initiating transcription of that DNA sequence.

Prokaryote. The term "prokaryote" is meant to include all organisms without a true nucleus, including bacteria.

Host. The term "host" is meant to include not only prokaryotes, but also such eukaryotes as yeast and filamentous fungi, as well as plant and animal cells. The terms includes organisms or cell that is the recipient of a replicable expression vehicle.

The present invention is based on the cloning and expression of two previously uncloned enzymes. Although heparinases II and III had been partially purified previously, no amino acid sequences were available. Specifically, the invention discloses the cloning, sequencing and expression of heparinases II and III from *Flavobacterium heparinum* and the use of a modified ribosome binding region for expression of these genes. In addition to the nucleotide sequences, the amino acid sequences of heparinases II and II are also provided. The invention further provides expressed heparinases I, II and III, as well as methods of expressing those enzymes.

Cloning was accomplished using degenerate and "guessmer" nucleotide primers derived from amino acid sequences of fragments of the heparinases, purified as described below in detail. The amino acid sequences were previously unavailable. Cloning was exceptionally difficult because of the unexpected problem of *F. heparinum* DNA toxicity in *E. coli*. The inventors discovered techniques for solving this problem, as described below in detail. Based on this disclosure, one skilled in the art can readily clone additional heparinases and other proteins from *F. heparinum* or from additional sources using the novel methods described within.

Expression of the heparinases is a further disclosure of the present invention. To express heparinases I, II and III, transcriptional and translational signals recognizable by an appropriate host are necessary. The cloned heparinases encoding sequences, obtained through the methods described above, and preferably in a double-stranded form, may be operably linked to sequences controlling transcriptional expression in an expression vector, and introduced into a host cell, either prokaryote or eukaryote, to produce recombinant heparinases or a functional derivative thereof. Depending upon which strand of the heparinases encoding sequence is operably linked to the sequences controlling transcriptional expression, it is also possible to express heparinases antisense RNA or a functional derivative thereof.

For the expression of heparinases I, II and III in *E. coli*, vectors were constructed wherein expression was driven by two repeats of the tac promoter. Modifications of the ribosome binding region of this promoter were made by introducing mutations with the polymerase chain reaction. In a preferred modification of the expression vector, the minimal consensus Shine-Delgarno sequence was improved by introducing a single mutation (AGGAA→AGGAG), which had the further advantage of decreasing the number of nucleotides between the Shine-Delgarno sequence and the ATG start codon. Further modifications were produced using PCR in which the gap between the Shine-Delgarno sequence and the start codon were further reduced. Using the same techniques, additional modifications in this region, including insertions and deletions, can be produced to create additional heparinase expression vectors. As a result, an expression vector for the expression of heparinases is provided which comprises a modified ribosome binding region containing a 5 base pair Shine-Dalgarno sequence, a 9 base pair spacer region between the Shine-Dalgarno sequence and the ATG start codon, and a recombinant nucleotide sequence encoding. Also provided are modifications to this vector comprising changing the length and sequence of the Shine-Dalgarno sequence, and also by reducing the spacing between the Shine-Dalgarno sequence and the start codon to 8, 7, 6, 5, 4 or fewer nucleotides. Methods of expressing the heparinases using these novel expression vectors comprise a preferred embodiment of the invention.

Expression of the heparinases in different hosts may result in different post-translational modifications which may alter the properties of the heparinases, or a functional derivative thereof, in eukaryotic cells, and especially mammalian, insect and yeast cells, Especially preferred eukaryotic hosts are mammalian cells either in vivo, in animals or in tissue culture. Mammalian cells provide post-translational modifications to recombinant heparinases which include folding and/or glycosylation at sites similar or identical to that found for the native heparinases. Most preferably, mammalian host cells include brain and neuroblastoma cells.

A nucleic acid molecule, such as DNA, is said to be "capable of expressing" a polypeptide if it contains expression control sequences which contain transcriptional regulatory information and such sequences are "operably linked" to the nucleotide sequence which encodes the polypeptide.

An operable linkage is a linkage in which a sequence is connected to a regulatory sequence (or sequences) in such a way as to place expression of the sequence under the influence or control of the regulatory sequence. Two DNA sequences (such as a heparinases encoding sequence and a promoter region sequence linked to the 5' end of the encoding sequence) are said to be operably linked if induction of promoter function results in the transcription of the heparinases encoding sequence mRNA and if the nature of the linkage between the two DNA sequences does not (1) result in the introduction of a frame-shift mutation, (2) interfere with the ability of the expression regulatory sequences to direct the expression of the heparinases, or (3) interfere with the ability of the heparinases template to be transcribed by the promoter region sequence. Thus, a promoter region would be operably linked to a DNA sequence if the promoter were capable of effecting transcription of that DNA sequence.

The precise nature of the regulatory regions needed for gene expression may vary between species or cell types, but in general includes, as necessary, 5' non-transcribing and 5' non-translating (non-coding) sequences involved with initiation of transcription and translation respectively, such as the TATA box, capping sequence, CAAT sequence, and the like. Especially, such 5' non-transcribing control sequences will include a region which contains a promoter for transcriptional control of the operably linked gene.

If desired, a fusion product of the heparinases may be constructed. For example, the sequence coding for heparinases may be linked to a signal sequence which will allow secretion of the protein from, or the compartmentalization of the protein in, a particular host. Such signal sequences maybe designed with or without specific protease sites such that the signal peptide sequence is amenable to subsequent removal. Alternatively, the native signal sequence for this protein may be used.

Transcriptional initiation regulatory signals can be selected which allow for repression or activation, so that expression of the operably linked genes can be modulated.

Based on this disclosure, one skilled in the art can readily place the sequences of the present invention in additional expression vectors and transform into a variety of bacteria to obtain recombinant heparinase II or heparinase III.

Once the vector or DNA sequence containing the construct(s) is prepared for expression, the DNA construct(s) is introduced into an appropriate host cell by any if a variety of suitable means, including transfection. After the introduction of the vector, recipient cells are grown in a selective medium, which selects for the growth of vector-containing cells. Expression of the cloned gene sequence(s) results in the production of heparinase I, II or III, or in the production of a fragment of one of these proteins. This expression can take place in a continuous manner in the transformed cells, or in a controlled manner, for example, expression which follows induction of differentiation of the transformed cells (for example, by administration of bromodeoxyuracil to neuroblastoma cells or the like).

The expressed protein is isolated and purified in accordance with conventional conditions, such as extraction, precipitation, chromatography, electrophoresis, or the like. Detailed procedures for the isolation of the heparinases is discussed in detail in the examples below.

The invention further provides functional derivatives of the sequences of heparinase II, heparinase III, and the modified ribosome binding site. As used herein, the term "functional derivative" is used to define any DNA sequence which is derived by the original DNA sequence and which still possesses the biological activities of the native parent molecule. A functional derivative can be an insertion, a deletion, or a substitution of one or more bases in the original DNA sequence. The substitutions can be such that they replace a native amino acid with another amino acid that does not substantially effect the functioning of the protein. Those skilled in the art will recognize that likely substitutions include positively the functioning of the protein, such as a small, neutrally charged amino acid replacing another small, neutrally charged amino acid. Those of skill in the art will recognize that functional derivatives of the heparinases can be prepared by mutagenesis of the DNA using one of the procedures known in the art, such as site-directed mutagenesis. In addition, random mutagenesis can be conducted and mutants retaining function can be obtained through appropriate screening.

The antibodies of the present invention include monoclonal and polyclonal antibodies, as well fragments of these antibodies. Fragments of the antibodies of the present invention include, but are not limited to, the Fab, the Fab2, and the Fc fragment.

The invention also provides hybridomas which are capable of producing the above-described antibodies. A hybridoma is an immortalized cell line which is capable of secreting a specific monoclonal antibody.

In general, techniques for preparing polyclonal and monoclonal antibodies as well as hybridomas capable of producing the desired antibody are well-known in the art (Campbell, A. M., "*Monoclonal Antibody Technology: Laboratory Techniques in Biochemistry and Molecular Biology,*" Elsevier Science Publishers, Amsterdam, The Netherlands (1984); St. Groth et al., *J. Immunol. Methods* 35:1–21 (1980)).

Any mammal which is known to produce antibodies can be immunized with the pseudogene polypeptide. Methods for immunization are well-known in the art. Such methods include subcutaneous or interperitoneal injection of the polypeptide. One skilled in the art will recognize that the amount of heparinase used for immunization will vary based on the animal which is immunized, the antigenicity of the peptide and the site of injection.

The protein which is used as an immunogen may be modified or administered in an adjuvant in order to increase the protein's antigenicity. Methods of increasing the antigenicity of a protein are well-known in the art and include, but are not limited to coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells.

Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124 (1988)).

Hybridomas secreting the desired antibodies are cloned and the class and subclass is determined using procedures known in the art (Campbell, A. M., *Monoclonal Antibody Technology: Laboratory Techniques in Biochemistry and Molecular Biology*, Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

The present invention further provides the above-described antibodies in detectably labelled form. Antibodies can be detectably labelled through the use of radioisotopes, affinity labels (such as biotin, avidin, etc.), enzymatic labels (such as horseradish peroxidase, alkaline phosphatase, etc.), fluorescent labels (such as FITC or rhodamine, etc.), paramagnetic atoms, chemiluminescent labels, and the like. Procedures for accomplishing such labelling are well-known in the art; for example, see Sternberger, L. A. et al., *J. Histochem. Cytochem.* 18:315 (1970); Byer, E. A. et al., *Meth. Enzym.* 62:308 (1979); Engval, E. et al., *Immunol.* 109:129 (1972); Goding, J. W., *J. Immunol. Meth.* 13:215 (1976).

The present invention further provides the above-described antibodies immobilized on a solid support. Examples of such solid supports include plastics, such as polycarbonate, complex carbohydrates such as agarose and sepharose, acrylic resins such as polyacrylamide and latex beads. Techniques for coupling antibodies to such solid supports are well known in the art (Weir et al., *Handbook of Experimental Immunology,* 4th Ed., Blackwell Scientific Publications, Oxford, England (1986)). The immobilized antibodies of the present invention can be used for immunoaffinity purification of heparinases.

Having now generally described the invention, the same will be understood by a series of specific examples, which are not intended to be limiting.

EXAMPLE 1

Purification of Heparinases

Heparin lyase enzymes were purified from cultures of *Flavobacterium heparinum*. *F. heparinum* was cultured in a 15 L computer-controlled fermenter using a variation of the defined nutrient medium described by Galliher et al., *Appl*

*Environ. Microbiol.* 41(2):360–365 (1981). Those fermentations designed to produce heparin lyases incorporate semi-purified heparin (Celsus Laboratories) in the media at a concentration of 1.0 g/L as the inducer of heparinase synthesis. Cells were harvested by centrifugation and the desired enzymes released from the periplasmic space by a variation of the osmotic shock procedure described by Zimmermann and Cooney, U.S. Pat. No. 5,262,325, herein incorporated by reference.

A semi-purified preparation of the heparinase enzymes was achieved by a modification of the procedure described by Zimmermann et al., U.S. Pat. No. 5,262,325. Proteins from the crude osmolate were adsorbed onto cation exchange resin (CBX, J. T. Baker) at a conductivity of 1–7 $\mu$mho. Unbound proteins from the extract were discarded and the resin packed into a chromatography column (5.0 cm i.d.×100 cm). The bound proteins eluted at a linear flow rate of 3.75 cm·min$^{-1}$ with step gradients of 0.01 M phosphate, 0.01 M phosphate/0.1 M sodium chloride, 0.01 M phosphate/0.25 M sodium chloride and 0.01 M phosphate/ 1.0 M sodium chloride, all at pH 7.0+/−0.1. Heparinase II elutes in the 0.1 M NaCl fraction, while heparinases 1 and 3 elute in the 0.25 M fraction.

Alternately, the 0.1 M sodium chloride step was eliminated and the three heparinases co-eluted with 0.25 M sodium chloride. The heparinase fractions were loaded directly onto a column containing cellufine sulfate (5.0 cm i.d.×30 cm, Amicon) and eluted at a linear flow rate of 2.50 cm·min$^{-1}$ with step gradients of 0.01 M phosphate, 0.01 M phosphate/0.2 M sodium chloride, 0.01 M phosphate/0.4 M sodium chloride and 0.01 M phosphate/1.0 M sodium chloride, all at pH 7.0+/−0.1. Heparinase II and 3 elute in the 0.2 M sodium chloride fraction while heparinase I elutes in the 0.4 M fraction.

The 0.2 M sodium chloride fraction from the cellufine sulfate column was diluted with 0.01 M sodium phosphate to give a conductance of less than 5 $\mu$mhos. The solution was further purified by loading the material onto a hydroxylapatite column (2.6 cm i.d.×20 cm) and eluting the bound protein at a linear flow rate of 1.0 cm·min-1 with step gradients of 0.01 M phosphate, 0.01 M phosphate/0.35 M sodium chloride, 0.01 M phosphate/0.45 M sodium chloride, 0.01 M phosphate/0.65 M sodium chloride and 0.01 M phosphate/1.0 M sodium chloride, all at pH 7.0+/−0.1. Heparinase III elutes in a single protein peak in the 0.45 M sodium chloride fraction while heparinase III elutes in a single protein peak in the 0.65 M sodium chloride fraction.

Heparinase I was further purified by loading material from the cellufine sulfate column, diluted to a conductivity less than 5 $\mu$mhos, onto a hydroxylapatite column (2.6 cm i.d.×20 cm) and eluting the bound protein at a linear flow rate of 1.0 cm·min$^{-1}$ with a linear gradient of phosphate (0.01 to 0.25 M) and sodium chloride (0.0 to 0.5 M). Heparinase I elutes in a single protein peak approximately mid-way through the gradient.

The heparinase enzymes obtained by this method were analyzed by SDS-PAGE using the technique of Laemmli, *Nature* 227: 680–685 (1970), and the gels quantified by a scanning densitometer (Bio-Rad, Model GS-670). Heparinases I, II and III displayed molecular weights of 42,500+/−2,000, 84,000+/−4,200 and 73,000+/−3,500 Daltons, respectively. All proteins displayed purities of greater than 99%. Purification results for the heparinase enzymes are shown in Table 1.

Heparinase activities were determined by the spectrophotometric assay described by Yang et al. A modification of this assay incorporating a reaction buffer comprised of 0.018 M Tris, 0.044 M sodium chloride and 1.5 g/L heparan sulfate at pH 7.5 was used to measure heparan sulfate degrading activity.

Recombinant heparinase I forms intracellular inclusion bodies which require denaturation and protein refolding to obtain active heparinase.

Two solvents, urea and guanidine hydrochloride, were examined as solubilizing agents. Of these, only guanidine HCl, at 6 M, was able to solubilize the heparinase 1 inclusion bodies. However, the highest degree of purification was obtained by sequentially washing the inclusion bodies in 3 M urea and 6 M guanidine HCl. The urea wash step served to removed contaminating *E. coli* proteins and cell debris prior to solubilizing of the aggregated heparinase I by guanidine HCl.

Recombinant heparinase I was prepared by growing *E. coli* Y1090(pGHep1), a strain harboring a plasmid containing the heparinase I gene expressed from tandem tac promoters, in Luria broth with 0.1 M IPTG. The cells were concentrated by centrifugation and resuspended in 1/10th volume buffer containing 0.01 M sodium phosphate and 0.2 M sodium chloride at pH 7.0. The cells were disrupted by sonication, 5 minutes with intermittent 30 second cycles, power setting #3 and the inclusion bodies concentrated by centrifugation, 7,000×g, 5 minutes. The pellets were washed two times with cold 3 M urea for 2 hours at pH, 7.0 and the insoluble material recovered by centrifugation. Heparinase I was unfolded in 6 M guanidine HCl containing 50 mM DTT and refolded by dialysis into 0.1 M ammonium sulfate. Additional contaminating proteins precipitated in the 0.1 M ammonium sulfate and could be removed by centrifugation. Heparinase I purified by this method had a specific activity of 42.21 IU/mg and was 90% pure by SDS-PAGE/scanning densitometry analysis. The enzyme can be further purified by cation exchange chromatography, as described above, yielding a heparinase I preparation that is more than 99% pure by SDS-PAGE/scanning densitometry analysis.

EXAMPLE 2

Characterization of Heparinases

The molecular weight and kinetic properties of the three heparinase enzymes have been accurately reported by Lohse and Linhardt, *J. Biol. Chem.* 267:24347–24355 (1992). However, an accurate characterization of the proteins' post-translational modifications had not been carried out. Heparinases I, II and III, purified as described herein, were analyzed for the presence of carbohydrate moieties. Solutions containing 2 ug of heparinases I, II and III and recombinant heparinase I were brought to pH 5.7 by adding 0.2 M sodium acetate. These protein samples underwent carbohydrate biotinylation following protocol 2a, described in the GlycoTrack kit (Oxford Glycosystems). 30 $\mu$l of each biotinylated protein solution was subjected to SDS-PAGE (10% gel) and transferred by electroblotting at 170 mA constant current to a nitrocellulose membrane. Detection of the biotinylated carbohydrate was accomplished by an alkaline phosphatase-specific color reaction after attachment of a streptavadin-alkaline phosphatase conjugate to the biotin groups. These analyses revealed that heparinases I and II are glycosylated and heparinase III and recombinant heparinase I are not.

Polyclonal antibodies generated in rabbits injected with wild type heparinase I could be fractionated into two populations as described below. It appears that one of these fractions recognizes a post-translational moiety common to proteins made in *F. heparinum*, while the other fraction specifically recognizes amino acid sequences contained in heparinase I. All heparinase enzymes made in *F. heparinum* were recognized by the "non-specific" antibodies but not heparinase made in *E. coli*. The most likely candidate for the non-protein antigenic determinant from heparinase I is the carbohydrate component; thus, the Western blot experiment indicates that all lyases made in *F. heparinum* are glycosylated.

Purified heparinases II and III were analyzed by the technique of Edman to determine the N-terminal amino acid residue of the mature protein. However, the Edman chemistry was unable to liberate an amino acid, indicating that a post-translational modification had occurred at the N-terminal amino acid of both heparinases. One nmol samples of heparinases II and III were used for deblocking with pyroglutamate aminopeptidase. Control samples were produced by mock deblocking 1 nmol protein samples without adding pyroglutamate aminopeptidase. All samples were placed in 10 mM $NH_4CO_3$, pH 7.5, and 10 mM DTT (100 µl final volume). To non-control samples, 1 mU of pyroglutamate aminopeptidase was added and all samples were incubated for 8 hr at 37° C. After incubation, an additional 0.5 mU of pyroglutamate aminopeptidase was added to non-control samples and all samples were incubated for an additional 16 h at 37° C.

Deblocking buffers were exchanged for 35% formic acid using a 10,000 Dalton cut-off Centricon unit and the sample was dried under vacuum. The samples were subjected to amino acid sequence analysis according to the method of Edman.

The properties of the three heparinase proteins from *Flavobacterium heparinum* are listed in Table 2.

Heparinases II and III were digested with cyanogen bromide in order to produce peptide fragments for isolation. The protein solutions (1–10 mg/ml protein concentration) were brought to a DTT concentration of 0.1 M, and incubated at 40° C. for 2 hr. The samples were frozen and lyophilized under vacuum. The pellet was resuspended in 70% formic acid, and nitrogen gas was bubbled through the solution to exclude oxygen. A stock solution of CNBr was made in 70% formic acid and the stock solution was bubbled with nitrogen gas and stored in the dark for short time periods. For addition of CNBr, a 500 to 1000 times molar excess of CNBr to methionine residues in the protein was used. The CNBr stock was added to the protein solutions, bubbled with nitrogen gas and the tube was sealed. The reaction tube was incubated at 24° C. for 20 hr, in the dark.

The samples were dried down partially under vacuum, water was added to the sample, and partial lyophilization was repeated. This washing procedure was repeated until the sample pellets were white. The peptide mixtures were solubilized in formic acid and applied to a Vydac $C_{18}$ reverse phase HPLC column (4.6 mm i.d.×30 cm) and individual peptide fragments eluted at a linear flow rate of 6.0 cm·min$^{-1}$ with a linear gradient of 10 to 90% acetonitrile in 1% trifluoroacetic acid. Fragments recovered from these reactions were subjected to amino acid sequence determination using an Applied Biosystems 745A Protein Sequencer. Three peptides isolated from heparinase II gave sequences: EFPEMYNLAAGR (SEQU ID NO:5), KPADIPEVKDGR (SEQU ID NO:6), and LAGDFVTGKILAQGFG PDNQTPDYTYL (SEQU ID NO:7) and were named peptides 2A, 2B and 2C respectively. Three peptides from heparinase III gave sequences: LIKNEVRWQLHRVK (SEQU ID NO:8), VLKASPPGEFHAQPDNGTFELFI (SEQU ID NO:9) and KALVHWFWPHKGYGYFDYGKDIN (SEQU ID NO:10) and were named peptides 3A, 3B and 3C, respectively.

EXAMPLE 3

Antibodies to the Heparinase Proteins

Heparinases I, II and III and recombinant heparinase I, purified as described herein, were used to generate polyclonal antibodies in rabbits. Each of heparinase I, II and III was carried through the following standard immunization procedure: The primary injection consisted of 0.5–1.0 mg of purified protein dissolved in 1 ml of sterile phosphate buffered Saline, which was homogenized with 1 ml of Freund's adjuvant (Cedarlane Laboratories Ltd.). This protein-adjuvant emulsion was used to inject New Zealand White female rabbits; 1 ml per rabbit, 0.5 ml per rear leg, i.m., in the thigh muscle near the hip. After 2 to 3 weeks, the rabbits were given an injection boost consisting of 0.5–1.0 mg of purified protein dissolved in sterile phosphate buffered Saline homogenized with 1 ml of incomplete Freund's adjuvant (Cedarlane Laboratories, Ltd.). Again after 2 to 3 weeks, the rabbits were given a third identical injection boost.

A blood sample was collected from each animal from the central artery of the ear approximately 10 days following the final injection boost. Serum was prepared by allowing the sample to clot for 2 hours at 22° C. followed by overnight incubation at 4° C., and clearing by centrifugation at 5,000 rpm for 10 min. The antisera were diluted 1:100,000 in Tris-buffered Saline (pH 7.5) and carried through Western blot analysis to identify those sera containing anti-heparinase I, II or III antibodies.

Antibodies generated against wild type heparinase I, but not recombinant heparinase I, displayed a high degree of cross reactivity against other *F. heparinum* proteins. This was likely due to the presence of an antigenic post-translational modification common to *F. heparinum* proteins but not found on proteins synthesized in *E. coli*. To explore this further, recombinant heparinase I was immobilized onto Sepharose beads and packed into a chromatography column. Purified anti-heparinase I (wild type) antibodies were loaded onto the column and the unbound fraction collected. Bound antibodies were eluted in 0.1 M glycine, pH 2.0. IgG was found in both the unbound and bound fractions and subsequently used in Western blot experiments. Antibody isolated from the unbound fraction non-specifically recognized *F. heparinum* proteins but no longer detected recombinant heparinase I (*E. coli*), while the antibody isolated from the bound fraction only recognized heparinase I, whether synthesized in *F. heparinum* or *E. coli*. This result indicated that, as hypothesized, two populations of antibodies are formed by exposure to the wild-type heparinase I antigen: one specific for the protein backbone and the other recognizing a post-translationally modified moiety common to F. heparinum proteins.

This finding provides both a means to purify specific anti-heparinase antibodies and a tool for characterizing the wild-type heparinase I protein.

EXAMPLE 4

Construction of a *F. heparinum* Gene Library

A *Flavobacterium heparinum* chromosomal DNA library was constructed in lambda phage DASHII. 0.4 ug of *F.* heparinum chromosomal DNA was partially digested with restriction enzyme Sau3A to produce a majority of fragments around 20 kb in size, as described in Maniatis, et al, Molecular Cloning Manual, Cold Spring Harbor (1982). This DNA was phenol/chloroform extracted, ethanol precipitated, ligated with λDASHII arms and packaged with packaging extracts from a λDASHII/BamHI Cloning Kit (Stratagene, La Jolla, Calif.). The library was titered at approximately $10^{-5}$ pfu/ml after packaging, amplified to $10^{-8}$ pfu/ml by the plate lysis method, and stored at $-70°$ C. as described by Silhavy, T. J., et al. in Experiments in Molecular Genetics, Cold Spring Harbor Laboratory, 1992.

The *F. heparinum* chromosomal library was titered to about 300 pfu/plate, overlaid on a lawn of *E. coli*, and allowed to transfect the cells overnight at 37° C., forming plaques. The phage plaques were transferred to nitrocellulose paper, and the phage DNA bound to the filters, as described in Maniatis, et al., ibid.

EXAMPLE 5

**A Modified Ribosome Binding Region for the Expression of *Flavobacterium heparinum* Glycosaminoglycan Lyases**

The gene for the mature heparinase I protein was cloned into the EcoRI site of the vector, pB9, where its expression was driven by two repeats of the tac promoter (from expression vector, pKK223-3, Brosius, and Holy, *Proc. Natl. Acad. Sci. USA* 81: 6929–6933 (1984)). In this vector, pBhep, the first codon, ATG, for heparinase 1 is separated by 10 nucleotides from a minimal Shine-Dalgarno sequence AGGA (Shine and Dalgarno, *Proc. Natl. Acad. Sci. USA* 71:1342–1346 (1974)), FIG. 1. This construct was transformed into the *E. coli* strain, JM109, grown at 37° C. and induced with 1 mM IPTG, 2 hours before harvesting. Cells were lysed by sonication, the cell membrane fraction was pelleted and the supernatant was saved. The membrane fraction was resuspended in 6M guanidine-HCl in order to solubilize inclusion bodies containing the recombinant heparinase I enzyme. The soluble heparinase I was refolded by diluting in 20 mM phosphate buffer. The enzyme activity was determined in the refolded pellet fraction, and in the supernatant fraction. Low levels of activity were detected in the supernatant and the pellet fractions. Analysis of the fractions by SDS-PAGE indicated that both fractions may contain minor bands corresponding to the recombinant heparinase I.

In an attempt to increase expression levels from pBhep, two mutations were introduced as indicated in FIG. 1. The mutations were produced to improve the level of translation of the heparinase I mRNA by increasing the length of the Shine-Dalgarno sequence and by decreasing the distance between the Shine-Dalgarno sequence and the ATG-start site. using PCR, a single base mutation converting an A to a G improved the Shine-Dalgarno sequence from a minimal AGGA sequence to AGGAG while decreasing the distance between the Shine-Dalgarno sequence and the translation start site from 10 to 9 base pairs. This construct was named pGhep. In the second construct, pΔ4hep, 4 nucleotides (AACA) were deleted using PCR, in order to lengthen the Shine-Dalgarno sequence to AGGAG as well as moving it to within 5 base pairs of the ATG-start site.

The different constructs were analyzed as described above. Refolded pellets from *E. coli* transformed with pGhep displayed approximately a 7x increase in heparinase I activity, as compared to refolded pellets from *E. coli* containing pBhep. On the other hand, *E. coil* containing pΔ4hep displayed 2–3 times less activity than the pBhep containing *E. coli* . The levels of heparinase 1 activity in the supernatants were similar.

Plasmid, pBhep, was digested with EcoRI and treated with S1 nuclease to form blunt-ended DNA. The plasmid DNA was then digested with BamHI and the single-stranded ends were made double-stranded by filling-in with Klenow fragment. The blunt-end DNA was ligated and transformed into *E. coli* strain FTB1. A plasmid which contained a unique BamHI site and no heparinase I gene DNA was purified from a kanamycin resistant colony and was designated plasmid, pGB. DNA sequence analysis revealed that plasmid pGB contained the modified ribosome binding site, shown in FIG. 1.

EXAMPLE 6

Nucleic Acid Encoding Heparinase II

Four "guessmer" oligonucleotides were designed using information from two peptide sequences 2A and 2B and use of the consensus codons for Flavobacterium, shown in Table 3. These were:

5'-GAATTCCCTGAGATGTACAATCTGGCCGC-3' (SEQU ID NO:1 1),

5'-CCGGCAGCCAGATTGTACATTTCAGG-3' (SEQU ID NO: 12),

5'-AAACCCGCCGACATTCCCGAAGTAAAAGA-3' (SEQU ID NO:13), and

5'-CGAAAGTCTTTTACTTCGGGAATGTCGGC-3' (SEQU ID NO: 14), named 2-1, 2-2, 2-3 and 2-4, respectively. The oligonucleotides were synthesized with a Bio/CAN (Mississauga, Ontario) peptide synthesizer. Pairs of these oligonucleotides were used as primers in PCR reactions. *F. heparinum* chromosomal DNA was digested with restriction endonucleases SalI, XbaI or NotI, and the fragmented DNA combined for use as the template DNA. Polymerase chain reaction mixtures were produced using the DNA Amplification Reagent Kit (Perkin Elmer Cetus, Norwalk, Conn.). The PCR amplifications were carried out in 100 μl reaction volume containing 50 mM KCl, 10 mM Tris HCl, pH 9, 0.1% Triton X-100, 1.5 mM $MgCl_2$, 0.2 mM of each of the four deoxyribose nucleotide triphosphates (dNTPs), 100 pmol of each primer, 10 ng of fragmented *F. heparinum* genomic DNA and 2.5 units of Taq polymerase (Bio/CAN Scientific Inc., Mississauga, Ontario).

The samples were placed on an automated heating block (DNA thermal cycler, Barnstead/Thermolyne Corporation, Dubuque, IA) programmed for step cycles of: denaturation temperature 92° C. (1 minute), annealing temperatures of 37° C., 42° C. or 45° C. (1 minute) and extension temperature 72° C. (2 minutes). These cycles were repeated 35 times. The resulting PCR products were analyzed on a 1.0% agarose gel containing 0.6 ug/ml ethidium bromide, as described by Maniatis, et al., ibid. DNA fragments were produced by oligonucleotides 2-2 and 2-3. The fragments, 250 bp and 350 bp in size, were first separated on 1% agarose gel electrophoresis, and the DNA extracted from using the GENECLEAN I kit (Bio/CAN Scientific, Mississauga, Ontario). Purified fragments were ligated into pTZ/PC (Tessier and Thomas, unpublished) previously digested with NotI, FIG. 2, and the ligation mixture used to transform *E. coli* FTB1, as described in Maniatis et al., ibid. All restriction enzymes and T4 DNA ligase were purchased from New England Biolabs (Mississauga, Ontario).

Strain FTB1 was constructed in our laboratory. The F' episome from the XL-1 Blue E. coli strain (Stratagene, La Jolla, Calif.), which carries the lac Iq repressor gene and produces 10 times more lac repressor than wild type E. coli, was moved, as described by J. Miller, Experiments in Molecular Genetics, Cold Spring Harbor Laboratory (1972), into the TB1 E. coli strain, described by Baker, T. A., et al., Proc. Natl. Acad. Sci. 81:6779–6783 (1984). The FTB 1 background permits a more stringent repression of transcription from plasmids carrying promoters with a lac operator (i.e. lac and Taq promoters). Colonies resulting from the transformation of FTB 1 were selected on LB agar containing ampicillin and screened using the blue/white screen provided by X-gal and IPTG included in the agar medium, as described by Maniatis, et al., ibid. Transformants were analyzed by colony cracking and mini-preparations of DNA were made for enzyme restriction analysis using the RPM kit (Bio/CAN Scientific Inc., Mississauga, Ontario). Ten plasmids contained inserts of the correct size, which were released upon digestion with EcoRI and HindIII.

DNA sequencing revealed that one of the plasmids, pCE14, contained a 350 bp PCR fragment had the expected DNA sequence as derived from peptide 2C. DNA sequences were determined by the dideoxy-chain termination method of Sanger et al., Proc. Natl. Acad. Sci. 74:5463–5467 (1978). Sequencing reactions were carried out with the Sequenase Kit (U.S. Biochemical Corp., Cleveland, Ohio) and $^{35}$S-dATP (Amersham Canada Ltd., Oakville, Ontario, Canada), as specified by the supplier.

The heparinase II gene was cloned from a F. heparinum chromosomal DNA library, FIG. 2, constructed as described above. Ten plaque-containing filters were hybridized with the DNA probe, produced from the gel purified insert of pCE14, which was labeled using a Random Labeling Kit (Boehringer Mannheim Canada, Laval, Quebec). Plaque hybridization was carried out, as described in Maniatis et al., ibid,, at 65° C. for 16 hours in a Tek Star hybridization oven (Bio/CAN Scientific, Mississauga, Ontario). Subsequent washes were performed at 65° C.: twice for 15 min. in 2× SSC, once in 2× SSC/0.1% SDS for 30 min. and once in 0.5× SSC/0.1% SDS for 15 min. Positive plaques were harvested using plastic micropipette tips and confirmed by dot blot analysis, as described by Maniatis et al., ibid. Six of the phages, which gave strong hybridization signals, were used for Southern hybridization analysis, as described by Southern, E.M., J. Mol. Biol. 98:503–517 (1975). This analysis showed that one phage, HIIS, contained a 5.5 kb XbaI DNA fragment which hybridized with the probe. Cloning the 5.5 kb XbaI fragment into the XbaI site of any of following vectors: pTZ/PC, pBluescript (Stratagene, La Jolla Calif.), pUC18 (described in Yanisch-Perron et al., Gene 33:103–119 (1985)), and pOK12 (described in Vierra and Messing, Gene 100:189–194 (1991)), was unsuccessful, even though the FTB1 background was used to repress plasmid promoter-derived transcription. Vector, pOK12, a low copy number plasmid derived from pACYC184 (approximately 10 copies/cell, Chang, A. C. Y. and Cohen, S. N., J. Bact. 134:1141–1156 (1978)) was used in an attempt to circumvent the toxic effects of a foreign DNA fragment in E. coli by minimizing the number of copies of the toxic foreign fragment. In addition, insertion of the entire NotI chromosomal DNA insert of the HIIS phage into plasmid pOK12 plasmid, was unsuccessful. It was concluded that this region of F. heparinum chromosome imparts a negative-selective effect on any E. coli cells that harbor it. This toxic affect had not been observed previously with other F. heparinum chromosomal DNA fragments.

A second strategy employed to circumvent the unexpected problem of F. heparinum DNA toxicity in E. coli was to digest the chromosomal DNA fragment with a restriction endonuclease which would divide the fragment, and if possible the heparinase II, gene into two pieces, FIG. 2. These fragments could be cloned individually. DNA sequence analysis of the PCR insert in plasmid, pCE14, demonstrated that BamHI and EcoRI sites were present in the insert. Hybridization experiments also demonstrated that the BamHI digested F. heparinum DNA in phage HIIS produced two bands 1.8 and 5.5 kb in size. Analysis of hybridization data indicated that the 1.8 kb band contains the 5' end and the 5.5 kb band contains the 3' end of the gene. Furthermore, a 5 kb EcoRI F. heparinum chromosomal DNA fragment hybridized with the PCR probe. The 1.8, 5, and 5.5 kb fragments containing heparinase II gene sequences were inserted into pBluescript, as described above. Two clones, pBSIB6-7 and pBSIB6-21, containing the 5.5 kb BamHI insert in different orientations were isolated and one plasmid, pBSIB213, was isolated which contained the 1.8 kb BamHI fragment. No clones containing the 5 kb EcoRI fragment were isolated, even though extensive screening of possible clones was done.

The molecular weight of heparinase II protein is approximately 84 kD, so the size of the corresponding gene would be approximately 2.4 kb. The 1.8 and 5.5 kb BamHI chromosomal DNA fragments could include the entire heparinase II gene. The plasmids pBSIB6-7, pBSIB6-21 and pBSIB2-13, FIG. 2, were used to produce nested deletions with the Erase-a-Base system (Promega Biotec, Madison Wis.). These plasmids were used as templates for DNA sequence analysis using universal and reverse primers and oligonucleotide primers derived from known heparinase II sequence. Because parts of the gene were relatively G-C rich and contained numerous strong, secondary structures, the sequence analysis was, at times, performed using reactions in which the dGTP was replaced by dITP. Analysis of the DNA sequence, FIG. 4, indicated that there was a single, continuous open reading frame containing codons for 772 amino acid residues, FIG. 5. Searching for a possible signal peptide sequence using Geneworks (Intelligenetics, Mountain View, Calif.) suggested that there are two possible sites for processing of the protein into a mature form: Q-26 (glutamine) and D-30 (aspartate). N-terminal amino acid sequencing of deblocked, processed heparinase II indicated that the mature protein begins with Q-26, and contains 747 amino acids with a calculated molecular weight of 84,545 Daltons, FIG. 5.

EXAMPLE 7

Expression of Heparinase II in E. coli

Figure 3:
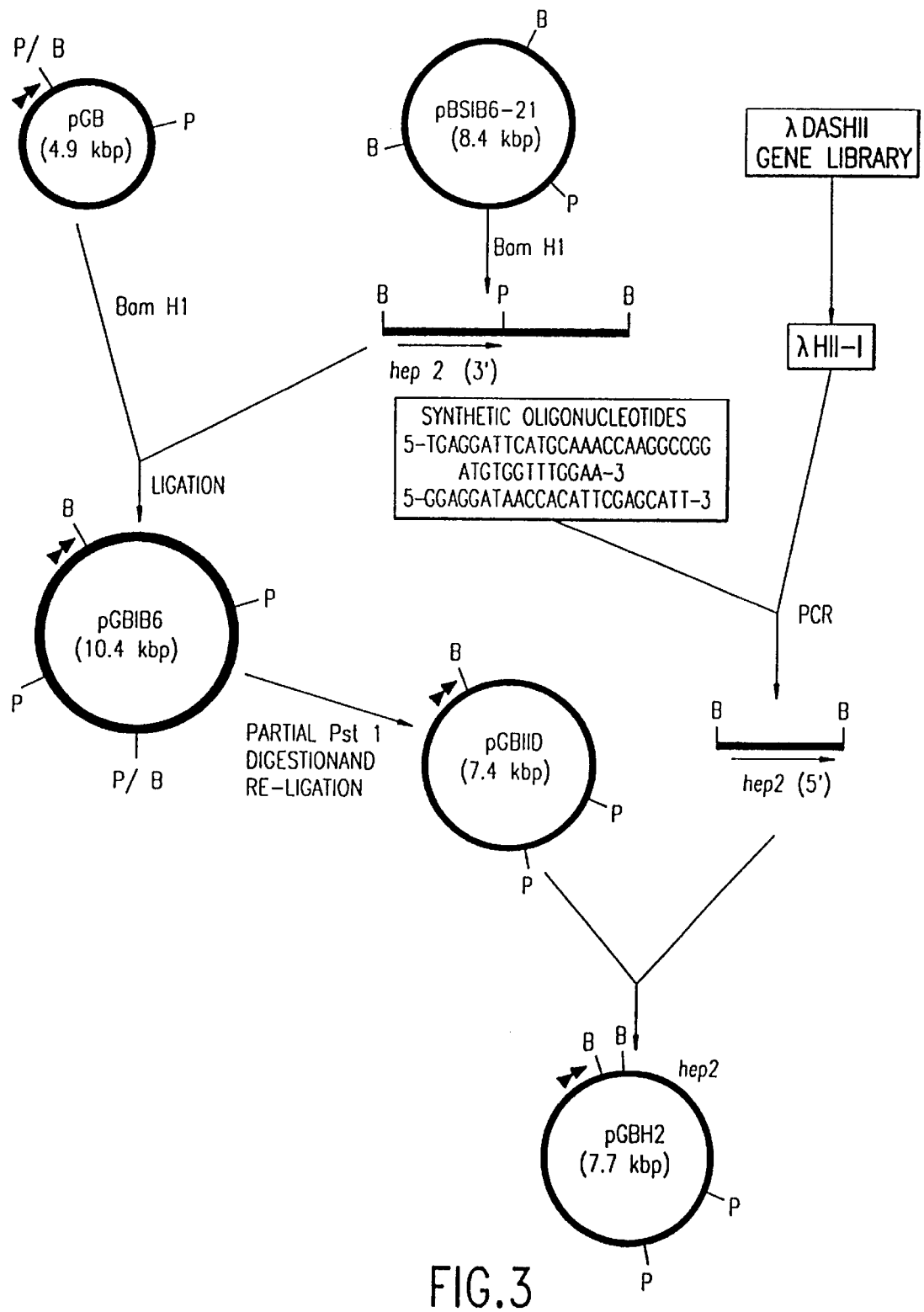
FIG. 3 shows the construction of pGBH2, a plasmid capable of directing the expression of active heparinase II in *E. coli* from tandem tac promoters (double arrow heads). Restriction sites are: B=BamHI, P=Pst I.

The vector, pGB, was used for heparinase II expression in E. coli, FIG. 3. pGB contains the modified ribosome binding region from pGhep, FIG. 1, and a unique BamHI site, whereby expression of a DNA fragment inserted into this site is driven by a double tac promoter. The vector also includes a kanamycin resistance gene, and the lac Iq gene to allow induction of transcription with IPTG. Initially, a gel purified 5.5 kb BamHI fragment from pBSIB6-21 was ligated with BamHI digested pGB and transformed into FTB 1, which was selected on LB agar with kanamycin. Six of the resulting colonies contained plasmids with inserts in the correct orientation for expression of the open reading frame. PstI digestion and religation of one of the plasmids, forming pGBIID, deleted 3.5 kb of the 5.5 kb BamHI fragment and removed a BamHI site leaving only one BamHI site directly after the Shine-Dalgarno sequence. Finally, two synthetic oligonucleotides were designed: 5'-TGAGGATTCATGCAAACCAAGGCCGATGT GGTTTGGAA-3' (SEQU ID NO:15), and 5'-GGAGGATAACCACATTCGAGCATT-3' (SEQU ID NO:16) for use in a PCR to produce a fragment containing a BamHI site and an ATG start codon upstream of the mature protein encoding sequence and a downstream BamHIsite, FIG. 3. Lambda clone HII-I, isolated at the same time as lambda clone HIIS, was used as template DNA.

Cloning the blunt-end PCR product into pTZ/PC was unsuccessful, using FTB1 as the host. Cloning the BamHI digested PCR product into the BamHI site of pBluescript, again using FTB1 as the host, resulted in the isolation of 2 plasmids containing the PCR fragment, after screening of 150 possible clones. One of these, pBSQTK-9, which was sequenced with reverse and universal primers, contained an accurate reproduction of the DNA sequence from the heparinase II gene. The BamHI digested PCR fragment from pBSQTK-9 was inserted into the BamHI site of pGBIID in such orientation that the ATG site was downstream of the Shine-Dalgarno sequence. This construct, pGBH2, placed the mature heparinase II gene under control of the tac promoters in pGB, FIG. 3. Strain $E.\ coli$ FTB1(pGBH2) was grown in LB medium containing 50 ug/ml kanamycin at 37° C. for 3 h. Induction of the tac promoter was achieved by adding 1 mmol IPTG and the culture placed at either room temperature or 30° C.

Heparin and heparan sulfate degrading activity was measured in the cultures after growth for 4 hours using the method described by Yang et al., ibid. Heparin degrading activities of 0.36 and 0.24 IU/mg protein and heparan sulfate degrading activities of 0.49 and 0.44 IU/mg protein were observed at room temperature and 30° C., respectively.

EXAMPLE 8

Nucleic Acid Encoding Heparinase III

The amino acid sequence information obtained from peptides derived from heparinase III, FIG. 9, purified as described herein, reverse translated into highly degenerate oligonucleotides. Therefore, a cloning strategy relying on the polymerase chain reaction amplification of a section of the heparinase III gene, using oligonucleotides synthesized on the basis of amino acid sequence information, required eliminating some of the DNA sequence possibilities. An assumed codon usage was calculated based on known DNA sequences for genes from other Flavobacterium species. Sequences for 17 genes were analyzed and a codon usage table was compiled, Table 3.

Four oligonucleotides were designed by choosing each codon according to the codon usage table. These were: 5'-GAATTCCATCAGTTTCAG CCGCATAAA-3' (SEQU ID NO: 17), 5'-GAATTCTTTATGCGGCTGAAACTGATG-3' (SEQU ID NO:18),5'-GAATTCCCGCCGGGCGAATTTCATGC-3' (SEQU ID NO: 19) and 5'-GAATTCGCATGAAATTCGCCCGGCCGG-3' (SEQU ID NO:20), and were named oligonucleotides 3-1, 3-2, 3-3 and 3-4, respectively. These oligonucleotides were used in all possible combinations, in an attempt to amplify a portion of the heparinase III gene using the polymerase chain reaction. The PCR amplifications were carried out as described above. Cycles of: denaturation temperature 92° C. (1 minute), annealing temperatures ranging from 37° . to 55° C., (1 minute) and extension temperature 72° C. (2 minutes) were repeated 35 times. Analysis of the PCR reactions as described above demonstrated that no DNA fragments were produced by these experiments.

A second set of oligonucleotides was synthesized and was comprised of 32 base sequences, in which the codon usage table was used to guess the third position of only half of the codons. The nucleotides within the parentheses indicate degeneracies of two or four bases at a single site. These were:

5'-GG(ACGT)GAATTCCATGCCCAGCC(ACGT)GA (CT)AATGG(ACGT)AC-3' (SEQU ID NO:21),

5'-GT(ACGT)CCATT(AG)TC(ACGT) GGCTGGGCATGAAATTC(ACGT)CC-3' (SEQU ID NO:22),

5'-GT(ACGT)CATCAGTT(CT)CAGCC(ACGT) CATAAAGG(ACGT)TATGG-3' (SEQU ID NO:23), and

5'-CCCATA(ACGT)CCTTTATG(ACGT)GGCTG(AG) AACTGATG(ACGT)AC-3' (SEQU ID NO:24), and were named oligonucleotides 3-5, 3-6, 3-7 and 3-8, respectively. These oligonucleotides were used in an attempt to amplify a portion of the heparinase III gene using the polymerase chain reaction, and the combination of 3-6 and 3-7 gave rise to a specific 983 bp PCR product. An attempt was made to clone this fragment by blunt end ligation into $E.\ Coli$ vector, pBluescript, as well as two specifically designed vectors for the cloning of PCR products, pTZ/PC and pCRII from the TA cloning™ kit (InVitrogen Corporation, San Diego, Calif.). All of these constructs were transformed into the FTB 1 $E.\ coli$ strain. Transformants were first analyzed by colony cracking, and subsequently minipreparations of DNA were made for enzyme restriction analysis. No clones containing this PCR fragment were isolated.

A third set of oligonucleotides was synthesized incorporating BamHI endonuclease sequences on the ends of the 3-6 and 3-7 oligonucleotide sequences. A 999 base pair DNA sequence was obtained using the polymerase chain reaction with $F.\ heparinum$ chromosomal DNA as the target. Attempts were made to clone the amplified DNA into the BamHI site of the high copy number plasmid pBluescript and the low copy number plasmids pBR322 and pACYC184. All of these constructs were again transformed into the FTB1 $E.\ coli$ strain. More than 500 candidates were screened, yet no transformants containing a plasmid harboring the $F.\ heparinum$ DNA were obtained. Once again, it was concluded that this region of $F.\ heparinum$ chromosome imparts a negative-selective effect on $E.\ coli$ cells that harbor it.

As in the case for isolation of the heparinase II gene, the PCR fragment was split in order to avoid the problem of foreign DNA toxicity. Digestion of the 981 bp BamHI-digested heparinase III PCR fragment with restriction endonuclease ClaI produced two fragments of 394 and 587 bp.

The amplified $F.\ heparinum$ region was treated with ClaI and the two fragments separated by agarose gel electrophoresis. The 587 and 394 base pair fragments were ligated separately into plasmid pBluescript that had been treated with restriction endonucleases BamHI and ClaI. In addition, the entire 981 bp PCR fragment was purified and ligated into BamHI cut pBluescript. The ligated plasmids were inserted into the XL-1 Blue $E.\ coli$. Transformants containing plasmids with inserts were selected on the basis of their ability to form white colonies on LB-agar plates containing X-gal, IPTG and 50 ug/ml ampicillin, as described by Maniatis.

Plasmid pFB1 containing the 587 bp *F. heparinum* DNA fragment and plasmid pFB2 containing the entire 981 base pair fragment were isolated by this method.

The XL-1 Blue strain, which, like strain FTB1, contains the lac Iq repressor gene on an F' episome, allowed for stable maintenance of the complete BamHI PCR fragment, unlike FUTB1. The reason for this discrepancy is not apparent from the genotypes of the two strains (i.e., both are rec A, etc.).

DNA sequence analysis of the *F heparinum* DNA in plasmid pFB1 showed that it contained a sequence encoding peptide Hep3-B while the F heparinum insert in plasmid pFB2 contained a DNA sequence encoding peptides Hep3-D and Hep3-B, FIG. 9. This analysis confirmed that these inserts were part of the gene encoding heparinase III.

Figure 6:
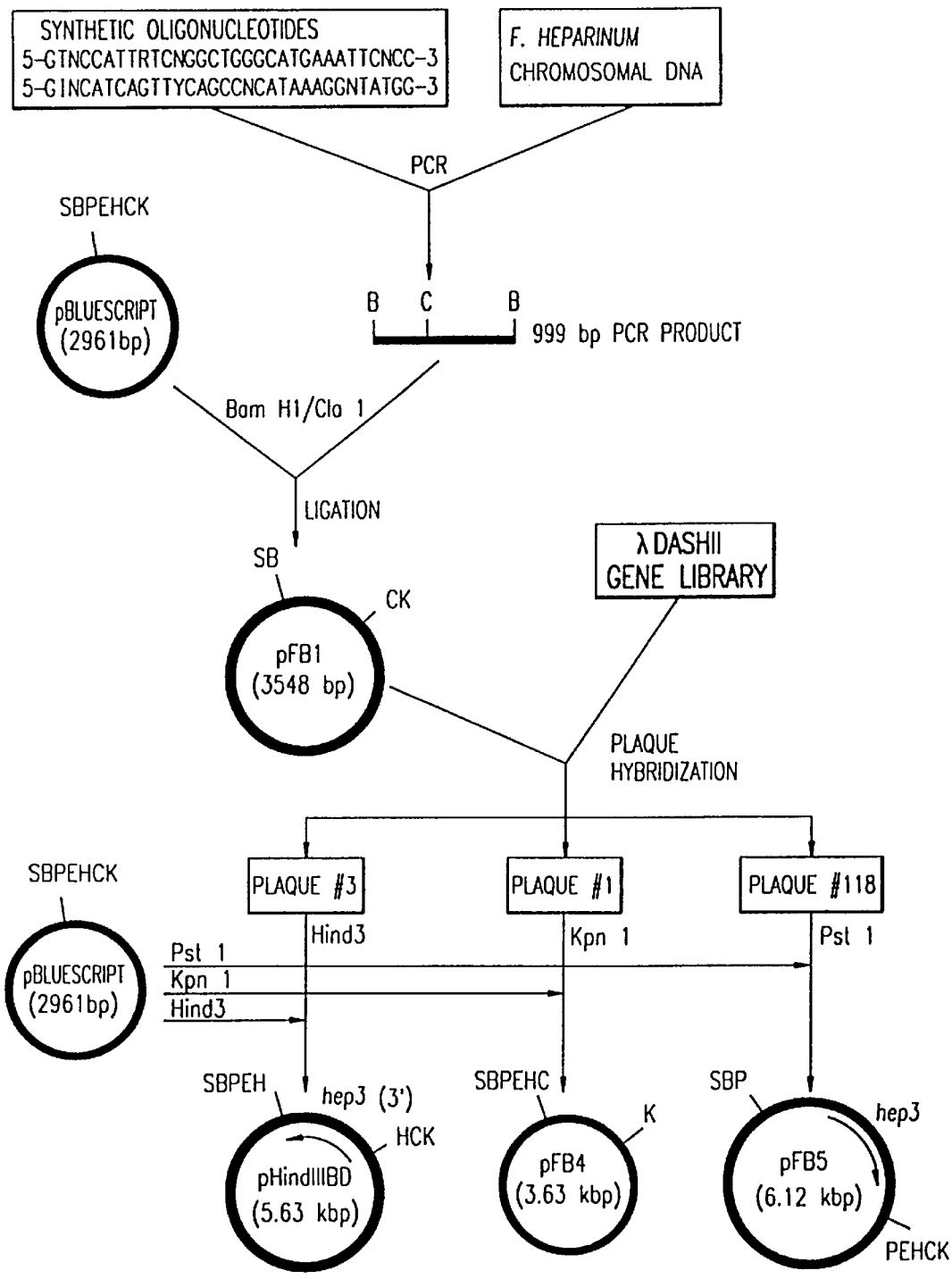
FIG. 6 shows the construction of plasmids used to sequence the heparinase III gene from *Flavobacterium heparinum*. Restriction sites are: S=SalI, B=BamHI, P=PstI, E=EcoRI, H=HindIII, C=ClaI and K=KpnI.

The PCR fragment insert in plasmid pFB1 was labeled with $^{32}$P-ATP using a Random Primed DNA Labeling kit (Boehringer Mannheim, Laval, Quebec), and was used to screen the *F. heparinum* λDASHII library, FIG. 6, constructed as described herein. The lambda library was plated out to obtain approximately 1500 plaques, which were transferred to nitrocellulose filters (Schleicher & Schuel, Keene, N.H.). The PCR probe was purified by ethanol precipitation. Plaque hybridization was carried out using the conditions described above. Eight positive lambda plaques were identified. Lambda DNA was isolated from lysed bacterial cultures as described in Maniatis and further analyzed by restriction analysis and by Southern blotting using a Hybond-N nylon membrane (Amersham Corporation, Arlington Heights, IL) following the protocol described in Maniatis. A 2.7 kilobase HindIII fragment from lambda plaque #3, which strongly hybridized to the PCR probe, was isolated and cloned in pBluescript, in the XL-1 Blue *E. coli* background, to yield plasmid pHindIIIBD, FIG. 6. This clone was further analyzed by DNA sequencing. The sequence data was obtained using successive nested deletions of pHindIIIBD generated with the Erase-a-Base System (Promega Corporation, Madison, Wis.) or sequenced using synthetic oligonucleotide primers.

Sequence analysis revealed a single continuous open reading frame, without a translational termination codon, of 1929 base pairs, corresponding to 643 amino acids. Further screening of the lambda library led to the identification of a 673 bp KpnI fragment which was similarly cloned into the KpnI site of pBluescript, creating plasmid pFB4. The termination codon was found within the KpnI fragment adding an extra 51 base pairs to the heparinase III gene and an additional 16 amino acid to the heparinase III protein. The complete heparinase III gene was later found to be included within a 3.2 kilobase PstI fragment from lambda plaque #118. The complete heparinase III gene from Flavobacterium is thus 1980 base pairs in length, FIG. 8, and encodes a 659 amino acid protein, FIG. 9. N-terminal amino acid sequencing of deblocked, processed heparinase III indicated that the mature protein begins with Q-25, and contains 635 amino acids with a calculated molecular weight of 73,135 Daltons, FIG. 9.

EXAMPLE 9

Expression of Heparinase III in *E. coli*

Figure 7:
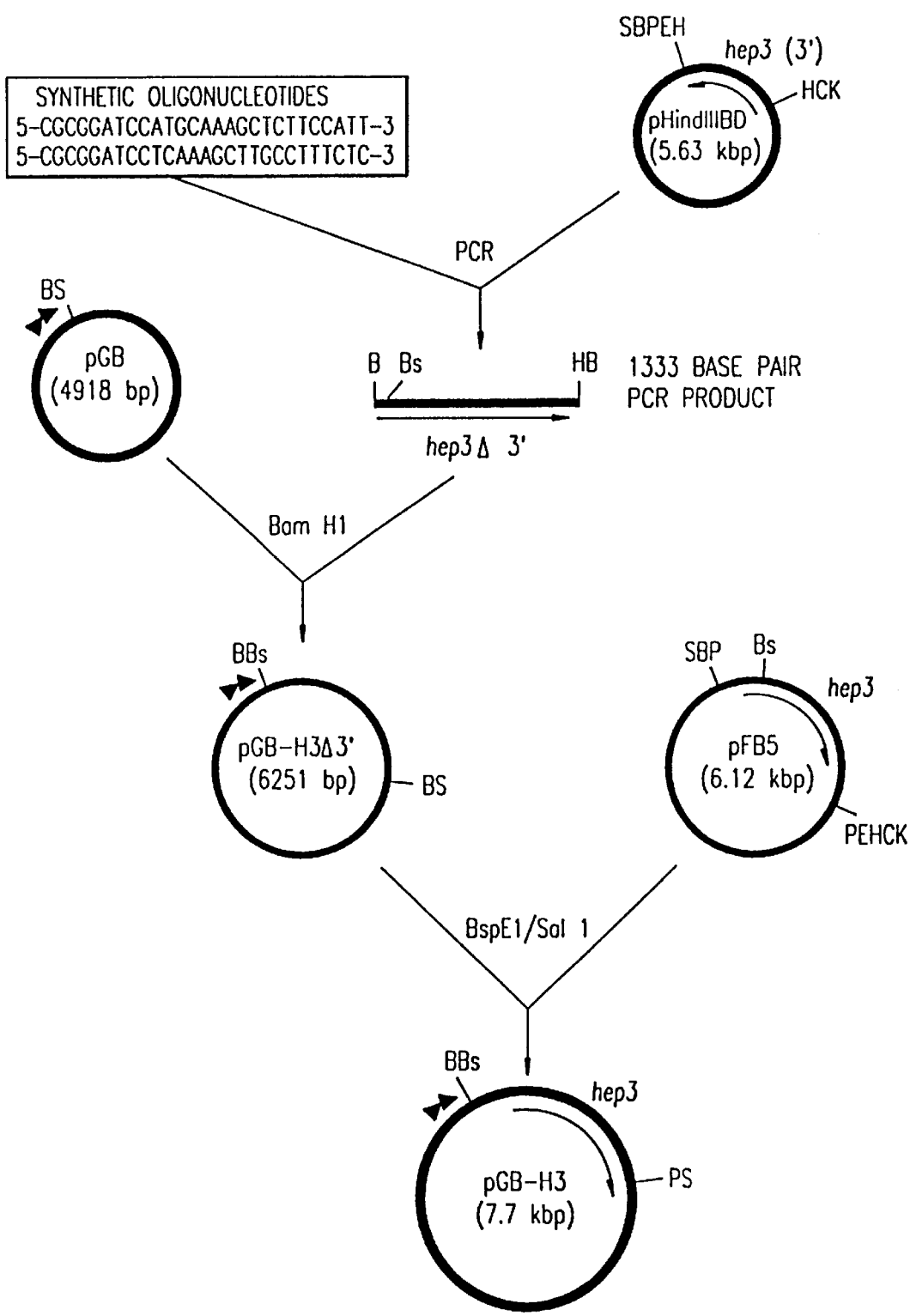
FIG. 7 shows the construction of pGBH3, a plasmid capable of directing the expression of active heparinase III in *E. coli* from a tandem taq promoter (double arrow heads). Restriction sites are: S=SalI, B=BamHI, P=PstI, E=EcoRI, H=HindIII, Bs=BspEI, C=ClaI and K=KpnI.

PCR was used to generate a mature, truncated heparinase III gene, which had 16 amino acids deleted from the carboxy-terminus of the protein. An oligonucleotide comprised of 5'-CGCGGATCCATGCAAAGCT CTTCCATT-3' (SEQU ID NO:25) was designed to insert an ATG start site immediately preceding the codon for the first amino acid (Q-25) of mature heparinase III, while an oligonucleotide comprised of 5'-CGCGGATCCTCA AAGCTTGCCTTTCTC-3' (SEQU ID NO:26), was designed to insert a termination codon after the last amino acid of the heparinase III gene on the 2.7 kb HindIII fragment. Both oligonucleotides also contained a BamHI site. Plasmid pHindIIIBD was used as the template in a PCR reaction with an annealing temperature of 50° C. A specific fragment of the expected size, 1857 base pairs, was obtained. This fragment encodes a protein of 620 amino acids with a calculated MW of 71,535 Da. It was isolated and inserted in the BamHI site of the expression vector pGB. This construct was named pGB-H3Δ3', FIG. 7.

To add the missing 3' region of heparinase III, the BspEI/SalI restriction fragment from pGB-H3Δ3' was removed and replaced with the BspEI/SalI fragment from pFB5. The construct containing the complete heparinase III gene was named pGBH3, FIG. 7. Recombinant heparinase III is a protein of 637 amino acids with a calculated molecular weight of 73,266 Daltons. *E. coli* strain XL-1 Blue(pGBH3) was grown at 37° C. in LB medium containing 75 ug/ml kanamycin to an $OD_{600}$ of 0.5, at which point the tac promoter from pGB was induced by the addition of 1 mM IPTG. Cultures were grown an additional 2–5 hours at either 23° C., 30° C. or 37° C. The cells were cooled on ice, concentrated by centrifugation and resuspended in cold PBS at 1/10th the original culture volume. Cells were lysed by sonication and cell debris removed by centrifugation at 10,000 ×g for 5 minutes. The pellet and supernatant fractions were analyzed for heparan sulfate degrading (heparinase III) activity. Heparan sulfate degrading activities of 1.29, 5.27 and 3.29 IU/ml were observed from cultures grown at 23°, 30° and 37° C., respectively.

The present invention describes a methodology for obtaining highly purified heparin and heparan sulfate degrading proteins by expressing the genes for these proteins in a suitable expression system and applying the steps of cell disruption, cation exchange chromatography, affinity chromatography and hydroxylapatite chromatography. Variations of these methods will be obvious to those skilled in the art from the foregoing detailed description of the invention. Such modifications are intended to come within the scope of the appended claims.

TABLE 1

Purification of heparinase enzymes from *Flavobacterium heparinum* fermentations

| sample | activity (IU) | specific activity (IU/mg) | yield (%) |
|---|---|---|---|
| fermentation | | | |
| heparin degrading | 39,700 | 1.06 | 100 |
| heparan sulfate degrading osmolate | 75,400 | ND | 100 |
| heparin degrading | 15,749 | ND | 40 |
| heparan sulfate degrading cation exchange | 42,000 | ND | 56 |
| heparin degrading | 12,757 | ND | 32 |
| heparan sulfate degrading cellufine sulfate | 27,540 | ND | 37 |
| heparin degrading | 8,190 | ND | 21 |
| heparan sulfate degrading hydroxylapatite | 9,328 | 30.8 | 12 |
| heparinase 1 | 7,150 | 115.3 | 18 |
| heparinase II | 2,049 | 28.41 | 3 |
| heparinase III | 5,150 | 44.46 | 7 |

TABLE 2

Propertied of heparinases from *Flavobacterium heparinum*

| sample | heparinase I | heparinase II | heparinase III |
| --- | --- | --- | --- |
| Km (μM) | 17.8 | 57.7 | 29.4 |
| Kcat (s$^{-1}$) | 157 | 23.3 | 164 |
| substrate | H | H and HS | HS |
| N-terminal peptide | QQKKSG | QTKADV | QSSSIT |
| glycosylation | yes | yes | maybe |

H - heparin, HS - heparin sulfate

TABLE 3

Codon usage table for Flavobacterium and *Escherichia Coli*

| amino acid | codon(s) | consensus codon E. coli | Flavobacterium |
| --- | --- | --- | --- |
| A | GCT, GCC, GCG, GCA | GCT | GCC |
| C | TGT, TGC | EITHER | EITHER |
| D | GAT, GAC | EITHER | EITHER |
| E | GAG, GAA | GAA | GAA |
| F | TTC, TTT | EITHER | TTT |
| G | GGC, GGA, GGG, GGT | GGC or GGT | GGC |
| H | CAC, CAT | CAT | CAT |
| I | ATC, ATA, ATT | ATA | ATC |
| K | AAA, AAG | AAA | AAA |
| L | CTT, CTA, CTG, TTG, TTA, CTC | CTG | CTG |
| M | ATG | ATG | ATG |
| N | AAC, AAT | AAC | AAT |
| P | CCC, CCT, CCA, CCG | CCG | CCG |
| Q | CAG, CAA | CAG | CAG |
| R | CGT, AGA, CGC, CGA, AGG, CGG | CGT | CGC |
| S | TCA, TCC, TCG, TCT, AGC, AGT | TCT | ? |
| T | ACG, ACC, ACT, ACA | ACC or ACT | ACC or ACA |
| V | GTC, GTA, GTT, GTG | GTT | ? |
| W | TGG | TGG | TGG |
| Y | TAC, TAT | EITHER | TAT |

We claim:

1. A recombinant nucleic acid sequence which encodes heparinase II from *Flavobacterium heparinum*.

2. The nucleic acid sequence of claim 1 comprising the sequence of SEQU ID NO:1.

3. The nucleic acid sequence of claim 1 further comprising a nucleic acid sequence capable of directing the expression of said heparinase.

4. The nucleic acid sequence of claim 3 comprising a modified ribosome binding region.

5. A host cell transformed with a vector comprising the nucleic acid sequence of claim 3, said host cell being capable of expressing heparinase II.

6. The host cell of claim 5, wherein said host cell is *E. coli*.

7. A recombinant nucleic acid sequence which encodes heparinase III from *Flavobacterium heparinum*.

8. The nucleic acid sequence of claim 7 comprising the sequence of SEQU ID NO:3.

9. The nucleic acid sequence of claim 7 further comprising a nucleic acid sequence capable of directing the expression of said heparinase.

10. The nucleic acid sequence of claim 9 comprising a modified ribosome binding region.

11. A host cell transformed with a vector comprising the nucleic acid sequence of claim 9, said host cell being capable of expressing heparinase III.

12. The host cell of claim 11, wherein said host cell is *E. coli*.

* * * * *